(12) United States Patent
Hodge et al.

(10) Patent No.: US 10,500,214 B2
(45) Date of Patent: *Dec. 10, 2019

(54) FORMULATIONS OF DEOXYCHOLIC ACID AND SALTS THEREOF

(71) Applicant: ALLERGAN SALES, LLC, Madison, NJ (US)

(72) Inventors: Robert Emil Hodge, Thousand Oaks, CA (US); Jeffrey Douglas Webster, Thousand Oaks, CA (US)

(73) Assignee: ALLERGAN SALES, LLC, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/103,505

(22) Filed: Aug. 14, 2018

(65) Prior Publication Data

US 2019/0038638 A1 Feb. 7, 2019

Related U.S. Application Data

(63) Continuation of application No. 15/650,556, filed on Jul. 14, 2017, now Pat. No. 10,071,105, which is a continuation of application No. 14/175,086, filed on Feb. 7, 2014, now Pat. No. 9,724,356, which is a continuation of application No. 13/733,729, filed on Jan. 3, 2013, now Pat. No. 9,186,364, which is a continuation of application No. 13/323,605, filed on Dec. 12, 2011, now Pat. No. 8,367,649, which is a continuation of application No. 12/716,070, filed on Mar. 2, 2010, now Pat. No. 8,101,593.

(60) Provisional application No. 61/274,129, filed on Mar. 3, 2009.

(51) Int. Cl.
*A61K 31/57* (2006.01)
*A61K 31/575* (2006.01)

(52) U.S. Cl.
CPC ............ *A61K 31/57* (2013.01); *A61K 31/575* (2013.01)

(58) Field of Classification Search
None
See application file for complete search history.

(56) References Cited

U.S. PATENT DOCUMENTS

| | | | |
|---|---|---|---|
| 4,113,882 A | 9/1978 | Okazaki et al. |
| 4,117,121 A | 9/1978 | Gallo-Torres et al. |
| 4,158,707 A | 6/1979 | Steffen et al. |
| 4,664,910 A | 5/1987 | Caserio et al. |
| 4,681,876 A | 7/1987 | Marples et al. |
| 4,722,888 A | 2/1988 | Broder et al. |
| 4,851,435 A | 7/1989 | Sauer et al. |
| 4,866,044 A | 9/1989 | Sato et al. |
| 4,994,439 A | 2/1991 | Longenecker et al. |
| 5,085,864 A | 2/1992 | Cannon et al. |
| 5,288,498 A | 2/1994 | Stanley et al. |
| 5,326,562 A | 7/1994 | Scott |
| 5,344,822 A | 9/1994 | Levine et al. |
| 5,371,104 A | 12/1994 | Feigenbaum |
| 5,376,646 A | 12/1994 | Pittrof et al. |
| 5,395,545 A | 3/1995 | Fischer et al. |
| 5,506,218 A | 4/1996 | Parker et al. |
| 5,603,932 A | 2/1997 | Blaas et al. |
| 5,616,342 A | 4/1997 | Lyons |
| 5,674,855 A | 10/1997 | Levine et al. |
| 5,747,066 A | 5/1998 | Pittrof et al. |
| 5,759,445 A | 6/1998 | Yamamoto et al. |
| 5,849,883 A | 12/1998 | Boone et al. |
| 5,863,554 A | 1/1999 | Illum |
| 5,876,721 A | 3/1999 | Alexander et al. |
| 5,891,083 A | 4/1999 | Capella et al. |
| 5,914,390 A | 6/1999 | Nathan et al. |
| 5,942,248 A | 8/1999 | Barnwell |
| 5,952,313 A | 9/1999 | Carlson |
| 5,952,392 A | 9/1999 | Katz et al. |
| 6,025,396 A | 2/2000 | Kim et al. |
| 6,120,805 A | 9/2000 | Spenlehauer et al. |
| 6,136,851 A | 10/2000 | Bonte et al. |
| 6,197,327 B1 | 3/2001 | Harrison et al. |
| 6,221,378 B1 | 4/2001 | Modi |
| 6,225,343 B1 | 5/2001 | Behl et al. |
| 6,251,428 B1 | 6/2001 | Yoo |
| 6,255,502 B1 | 7/2001 | Penkler et al. |
| 6,294,192 B1 | 9/2001 | Patel et al. |
| 6,313,128 B1 | 11/2001 | Blanc-Ferras et al. |
| 6,315,984 B1 | 11/2001 | Modi |
| 6,342,489 B1 | 1/2002 | Palmieri et al. |

(Continued)

FOREIGN PATENT DOCUMENTS

| | | |
|---|---|---|
| CA | 2033725 C | 5/2001 |
| CA | 2551474 A1 | 7/2005 |

(Continued)

OTHER PUBLICATIONS

U.S. Appl. No. 11/710,601, filed Feb. 23, 2007, Burkhart et al.
U.S. Appl. No. 12/397,229, filed Mar. 3, 2009, Hodge et al.
U.S. Appl. No. 13/753,366, filed Jan. 29, 2013, Hodge et al.
"Evaluation of Safety and Efficacy of ATX-101 in the Reduction of Submental Fat," NCT01294644, Feb. 28, 2011.
"Health Alert: Lipostabil" http://kyw.com/healtn/local.sup.--story.sub.--336152/06.html, Dec. 2, 2002.

(Continued)

*Primary Examiner* — Craig D Ricci
(74) *Attorney, Agent, or Firm* — Foley & Lardner LLP

(57) ABSTRACT

The present application is directed to an aqueous pharmaceutical formulation comprising less than about 5% w/v sodium deoxycholate maintained at a pH sufficient to substantially inhibit precipitation of the sodium deoxycholate. Also disclosed herein, are methods for inhibiting precipitation of sodium deoxycholate in an aqueous solution comprising less than about 5% w/v of sodium deoxycholate, said method comprising maintaining pH of the solution of from at least about 8.0 to about 8.5.

6 Claims, 8 Drawing Sheets

(56) References Cited

U.S. PATENT DOCUMENTS

| | | |
|---|---|---|
| 6,350,458 B1 | 2/2002 | Modi |
| 6,375,975 B1 | 4/2002 | Modi |
| 6,383,471 B1 | 5/2002 | Chen et al. |
| 6,416,779 B1 | 7/2002 | D'Augustine et al. |
| 6,417,179 B1 | 7/2002 | Burkhart et al. |
| 6,451,286 B1 | 9/2002 | Modi |
| 6,489,312 B1 | 12/2002 | Stogniew et al. |
| 6,537,561 B1 | 3/2003 | Fukui et al. |
| 6,544,972 B1 | 4/2003 | Steer et al. |
| 6,573,299 B1 | 6/2003 | Petrus |
| 6,663,885 B1 | 12/2003 | Hager et al. |
| 6,713,470 B2 | 3/2004 | Jackson |
| 6,828,155 B1 | 12/2004 | Kaneko et al. |
| 6,849,263 B2 | 2/2005 | Modi |
| 6,884,768 B2 | 4/2005 | Kimura et al. |
| 7,052,716 B1 | 5/2006 | Lanzendorfer et al. |
| 7,166,299 B2 | 1/2007 | Yoo |
| 7,226,775 B2 | 6/2007 | Mapleson et al. |
| 7,303,768 B2 | 12/2007 | Yoo |
| 7,538,093 B2 | 5/2009 | Engler et al. |
| 7,622,130 B2 | 11/2009 | Kolodney et al. |
| 7,754,230 B2 | 7/2010 | Kolodney et al. |
| 8,101,593 B2 | 1/2012 | Hodge et al. |
| 8,258,146 B2 | 9/2012 | Morita et al. |
| 8,298,556 B2 | 10/2012 | Kolodney et al. |
| 8,367,649 B2 | 2/2013 | Hodge et al. |
| 8,653,058 B2 | 2/2014 | Hodge et al. |
| 8,846,066 B2 | 9/2014 | Kolodney et al. |
| 9,186,364 B2 | 11/2015 | Hodge et al. |
| 9,636,349 B2 | 5/2017 | Moriarty et al. |
| 2001/0051595 A1 | 12/2001 | Lyons et al. |
| 2002/0028766 A1 | 3/2002 | Papadimitriou |
| 2002/0031558 A1 | 3/2002 | Yoo |
| 2002/0032159 A1 | 3/2002 | Maruyama et al. |
| 2002/0058010 A1 | 5/2002 | Picard-Lesboueyries et al. |
| 2002/0107917 A1 | 8/2002 | De Tommaso |
| 2002/0168402 A1 | 11/2002 | Kipp et al. |
| 2003/0027833 A1 | 2/2003 | Cleary et al. |
| 2003/0035831 A1 | 2/2003 | Modi |
| 2003/0054981 A1 | 3/2003 | Milton et al. |
| 2003/0064097 A1 | 4/2003 | Patel et al. |
| 2003/0072807 A1 | 4/2003 | Wong et al. |
| 2003/0077329 A1 | 4/2003 | Kipp et al. |
| 2003/0161886 A1 | 8/2003 | Dickinson et al. |
| 2003/0186933 A1 | 10/2003 | Yoo |
| 2003/0219472 A1 | 11/2003 | Pauletti et al. |
| 2004/0022862 A1 | 2/2004 | Kipp et al. |
| 2004/0038952 A1 | 2/2004 | Feher |
| 2004/0067919 A1 | 4/2004 | Jee |
| 2004/0096494 A1 | 5/2004 | Siekmann et al. |
| 2004/0101569 A1 | 5/2004 | Rang |
| 2004/0115255 A1 | 6/2004 | Leigh et al. |
| 2004/0118412 A1 | 6/2004 | Piletti-Reyes |
| 2004/0141949 A1 | 7/2004 | Rosenthal et al. |
| 2004/0161407 A1 | 8/2004 | Kimura et al. |
| 2004/0201117 A1 | 10/2004 | Anderson |
| 2004/0213855 A1 | 10/2004 | Pettersson et al. |
| 2004/0220283 A1 | 11/2004 | Zhang et al. |
| 2005/0019404 A1 | 1/2005 | Sung et al. |
| 2005/0048126 A1 | 3/2005 | Rabinow et al. |
| 2005/0079228 A1 | 4/2005 | Jaiswal et al. |
| 2005/0089555 A1 | 4/2005 | Boderke et al. |
| 2005/0123582 A1 | 6/2005 | Sung et al. |
| 2005/0143347 A1 | 6/2005 | Boderke et al. |
| 2005/0158408 A1 | 7/2005 | Yoo |
| 2005/0163821 A1 | 7/2005 | Sung et al. |
| 2005/0261258 A1 | 11/2005 | Kolodney et al. |
| 2005/0266065 A1 | 12/2005 | Perrier et al. |
| 2005/0267080 A1 | 12/2005 | Kolodney et al. |
| 2005/0287199 A1 | 12/2005 | Denney et al. |
| 2006/0074057 A1 | 4/2006 | Marchewitz |
| 2006/0127468 A1 | 6/2006 | Kolodney et al. |
| 2006/0154906 A1 | 7/2006 | Kolodney et al. |
| 2006/0222673 A1 | 10/2006 | Chern et al. |
| 2006/0222695 A1 | 10/2006 | Zadini et al. |
| 2008/0318870 A1 | 12/2008 | Moriarty et al. |
| 2009/0270642 A1 | 10/2009 | Prasad et al. |
| 2009/0275545 A1 | 11/2009 | Boderke et al. |
| 2010/0048527 A1 | 2/2010 | Kolodney et al. |
| 2010/0292650 A1 | 11/2010 | Kolodney et al. |
| 2011/0002896 A1 | 1/2011 | Kolodney et al. |
| 2011/0218181 A1 | 9/2011 | Hodge et al. |
| 2012/0237492 A1 | 9/2012 | Walker |
| 2013/0109282 A1 | 5/2013 | Lewkoski et al. |
| 2013/0190282 A1 | 7/2013 | Hodge et al. |
| 2014/0004206 A1 | 1/2014 | Kolodney et al. |
| 2014/0148429 A1 | 5/2014 | Hodge et al. |
| 2014/0155364 A1 | 6/2014 | Hodge et al. |
| 2015/0051182 A1 | 2/2015 | Kolodney et al. |
| 2017/0319601 A1 | 11/2017 | Walker |

FOREIGN PATENT DOCUMENTS

| | | |
|---|---|---|
| CN | 1348360 A | 5/2002 |
| EP | 0 208 519 A2 | 1/1987 |
| EP | 0 408 174 A1 | 1/1991 |
| EP | 0 426 029 A1 | 5/1991 |
| EP | 0 439 042 B1 | 6/1995 |
| EP | 0 439 513 B1 | 3/1996 |
| EP | 1 111 390 | 6/2001 |
| EP | 0 730 860 B1 | 1/2002 |
| EP | 0 806 940 B1 | 4/2003 |
| EP | 1 005 324 B1 | 3/2005 |
| EP | 2 561 876 A1 | 2/2013 |
| JP | 61-158995 | 7/1986 |
| JP | 03-048622 | 3/1991 |
| JP | 04-235918 | 8/1992 |
| JP | 11-240835 | 9/1999 |
| JP | 2007-515439 | 6/2007 |
| JP | 2007-515494 | 6/2007 |
| JP | 2007-538104 | 12/2007 |
| JP | 2008-530005 A | 8/2008 |
| JP | 2010-222283 | 10/2010 |
| KR | 10-2007-0110351 | 11/2007 |
| WO | WO-90/12583 A1 | 11/1990 |
| WO | WO-93/05811 A1 | 4/1993 |
| WO | WO-94/04177 A1 | 3/1994 |
| WO | WO-99/15152 A1 | 4/1999 |
| WO | WO-00/04875 A1 | 2/2000 |
| WO | WO-00/13029 | 3/2000 |
| WO | WO-01/70151 A1 | 9/2001 |
| WO | WO-02/058610 A1 | 8/2002 |
| WO | WO-03/018134 A2 | 3/2003 |
| WO | WO-03/082340 A1 | 10/2003 |
| WO | WO-03/094894 A1 | 11/2003 |
| WO | WO-2004/010941 A2 | 2/2004 |
| WO | WO-2004/039326 A2 | 5/2004 |
| WO | WO-2005/020894 A2 | 3/2005 |
| WO | WO-2005/061004 A1 | 7/2005 |
| WO | WO-2005/063169 A2 | 7/2005 |
| WO | WO-2005/063205 | 7/2005 |
| WO | WO-2005/112942 | 12/2005 |
| WO | WO-2005/112942 A1 | 12/2005 |
| WO | WO-2005/117832 A1 | 12/2005 |
| WO | WO-2005/117900 A1 | 12/2005 |
| WO | WO-2006/007675 A1 | 1/2006 |
| WO | WO-2006/086038 A1 | 8/2006 |
| WO | WO-2006/133160 A2 | 12/2006 |
| WO | WO-2011/07570 A2 | 6/2011 |
| WO | WO-2012/112940 A1 | 8/2012 |

OTHER PUBLICATIONS

"Lose those love handles" A CBS HealthWatch Special Report http://cbsnewyork.com/healthwatch/local.sub.--story.sub.--329141707. html, Nov. 25, 2002.

"Love handles can be shrunk without surgery" http://www.macleans. ca/topstories/health/article.jsp?content=20040225.sub .--090843. sub.--4800, Feb. 25, 2004.

"Deoxycholic acid", Product Information, SIGMA, 2002.

Ablon, et al., "Treatment of lower eyelid fat pads using phosphatidylcholine: clinical trial and review," Derm. Surgery, (2004), 30(3):422-427.

(56) References Cited

OTHER PUBLICATIONS

Alkan-Onyuksel H, Ramakrishnan S, Chai HB, Pezzuto JM. A mixed micellar formulation suitable for the parenteral administration of taxol. Pharm Res 1994, 11:206-12.

Almgren M. Mixed micelles and other structures in the solubilization of bilayer lipid membranes by surfactants. Biochim Biophys Acta 2000,1508:146-63.

Asaadi M, Salas AP, Motamedi B. Mesoplasty: a new approach to non-surgicalliposculpture. Plastic Surgery 2004, Oct. 10, 2004, Philadelphia, PA.

ASAPS. American Society for Aesthetic Plastic Surgery. Lipoplasty (liposuction) without surgery?, Oct. 2002.

Avissar et al., "Plasma Selenium-dependent Glutathione Peroxidase," J. Biol. Chem., (1989), 264(27):15850-15855.

Banerjee P, Joo JB, Buse JT, Dawson G. Differential solubilization of lipids along with membrane proteins by different classes of detergents. Chem Phys Lipids 1995, 77:65-78.

Bates B. 'Fat dissolving' substance injects CCs of controversy. Skin and Allergy News 2003,34.

Baumann LS. Phosphatidylcholine. Skin and Allergy News 2003, 34.

BAYER_ Press Release, "First Patients enrolled in EU Phase III Clinical Development Program to evaluate ATX-101 for reduction of Submental Fat," (2008).

Bellman B. Phosphatidylcholine reaction. Skin and Allergy News 2003, 34.

Bril et al., "Fractionation of spinach chloroplasts with sodium deoxycholate," Biochim. Biophys. Acta, (1969), 172:345-348.

Bryant, R., Controversial mesotherapy: could it be the next botox. Dermatology Times, Dec. 2004, 1-2.

Buko V, Lukivskaya O, Nikitin V, I arasov Y, Zavodnick L, Borodinsky A, Gorenshtein B, Janz B, Gundermann K-J, Schumacher R. Hepatic and pancreatic effects of polyenoylphosphatidylcholine in rats with alloxan-induced diabetes. Cell Biochem Function 14:131-7, 1996.

Canty D, Zeisel S, Jolitz A. Lecithin and choline: research update on health and nutrition. Fort Wayne, IN: Central Soya Company, Inc., 1998.

Chalmers K. Fat loss a needle away. http://surgerynews.net/news/0204/meso020402.htm, Feb. 1, 2004.

Chen et al., "Formation of Sodium Dodecyl Sulfate-stable Fibronectin Multimers," J Biol. Chem., (1996), 271 (15):9084-9089.

Cho et al.,"α-Lipoic Acid Inhibits Adipocyte Differentiation by Regulating Pro-adipogenic Transcription Factors via Mitogen-activated Protein Kinase Pathways," J. Biol. Chem, 2003, 278(37):34823-34833.

Complaint for Patent Infringement, *Kythera Biopharmaceuticals, Inc. v. Slayback Pharma LLC*, Filed Nov. 9, 2018.

Crowley et al., "The NAD+ precursors, nicotinic acid and nicotinamide protect cells against apoptosis induced by a multiple stress inducer, deoxycholate," Cell Death and Differentiation, (2000), 7:314-326.

Davidson et al. "Limitations of phosphatidylcholine/deoxycholate mixtures for the analysis of phospholipase A2 inhibition and activation: illustration with annexins." Biochimica et Biophysica Acta, 1992, 1127(3):270-276.

Duncan D. "Injection Lypolysis for Body Contouring," Springer Berlin Heidelberg, (2010), 59-70.

Duncan et al., "Fat Reduction Using Phosphatidylcholine/Sodium Deoxycholate Injections: Standard of Practice", Aesthetic Plastic Surgery, 2008, 32(6):858-872.

Duncan et al., "Lipodissolve for Subcutaneous Fat Reduction and Skin Retraction," Aesthetic Surgery Journal, (2005), 25(5):530-543.

Duncan et al.: "Injectable therapies for localized fat loss: state of the art.", Clinics in Plastic Surgery, 2011, LNKDPUBMED:21824545, vol. 38, No. 3, 2011, pp. 489-501.

Durr M, Hager J, Lohr JP. Investigation on mixed micelle and liposome preparations for parental use on soya phosphatidylcholine. EurJ Pharm Biopharm 1994, 40: 147-56.

Ebihara L, Hall JE, MacDonald RC, Mcintosh TJ, Simon SA. Effect of benzyl alcohol on lipid bilayers. A comparisons of bilayer systems. Biophys J 1979,28:185-96.

Engelke M, Jessel R, Wiechmann A, Diehl HA. Effect of inhalation anaesthetics on the phase behaviour, permeability and order of phosphatidylcholine bilayers. Biophys Chem 1997,67:127-38.

FDA Guidance for Industry, Q6B Specifications: Test Procedures and Acceptance Criteria for Biotechnological/Biological Products, U.S. Department of Health and Human Services Food and Drug Administration, Aug. 1999.

FDA news release: "FDA issues warning letters for drugs promoted in fat elimination procedure", 2010, Retrieved from the Internet: URL:http://www.fda.gov/NewsEvents/Newsroom/PressAnnouncements/ucm207453.htm [retrieved on Oct. 18, 2011].

Fit. The first UK injection technique recommendations. Becton, Dickinson and Company. 2010;1-13.

Gething et al., "Purification of fusion protein of Sendai virus: Analysis of the NH2-terminal sequence generated during precursor activation," Proc. Natl. Acad. Sci., (1978), 75(6):2737-2740.

Goldman L, Bennet JC, Cecil RL. Cecil Textbook of Medicine. St. Louis, MO: W.B. Saunders Co., 2001.

Gordon LM, Sauerheber RD, Esgate JA, Dipple I, Marchmont RJ, Houslay MD. The increase in bilayer fluidity of rat liver plasma membranes achieved by the local anesthetic benzyl alcohol affects the activity of intrinsic membrane enzymes. J Biol Chem 1980, 255:4519-27.

Gustafson C, Tagesson C. Influence of organic solvent mixtures on biological membranes. Br J Ind Med 1985, 42:591-5.

Hammad MA, Muller BW. Increasing drug solubility by means of bile salt-phosphatidylcholine-based mixed micelles. Eur J Pharm Biopharm 1998, 46:361-7.

Hasengschwandtner, F. "Phosphatidylcholine treatment to induce lipolysis," Journal of Cosmetic Dermatology, (2005), 4:308-313.

Heerklotz H, Seelig J. Correlation of membrane/water partition coefficients of detergents with the critical micelle concentration. Biophys J 2000, 78:2435-40.

Hexsel, et al., "Phosphatidylcholine in the treatment of localized fat," J. Drugs Dermatol., (2003), 2(5):511-518.

Hofmann et al., "Physicochemical properties of bile acids and their relationship to biological properties: an overview of the problem," J. Lipid Res., (1984), 25:1477-1489.

Hofmann et al., "Bile acid solubility and precipitation in vitro and in vivo: the role of conjugation, pH, and Ca2+ ions", Journal of Lipid Research, vol. 33, pp. 617-626 (1992).

Hutchison, ABC News Medical Unit: "Does Question Bayer's Injection for Dissolving Double Chin", 2011, Retrieved from Internet: URL:http://abcnews.go.com/Health/WellnessNews/bayer-tests-fat-loss-injection-double-chin/story?id=12600333, [retrieved on May 22, 2014].

Igimi et al., "pH-Solubility relations of chenodeoxycholic and ursodeoxycholic acids: physical-chemical basis for dissimilar solution and membrane phenomena", Journal of Lipid Research, vol. 21, pp. 72-90 (1980).

Jones MN. Surfactants in membrane solubilisation. Int J Pharm 1999, 177:137-59.

JP Office Action for Application No. 2014-527128 dated Jun. 23, 2015.

Kavvanaka et al., NASH, Japanese Journal of Liver, Biliary tract, and Pancreas, 2002, 44(4):521-526.

Kern, et al., "Regulation of Lipoprotein Lipase Immunoreactive Mass in Isolated Human Adipocytes", J. Clin. Invest., vol. 81, pp. 398-406; (1988).

Klein, et al., "A New Method to Quantify the Effect After Subcutaneous Injection of Lipolytic Substances," Aesth Plast Surg., (2008), 32:667-672.

Kolonin, et al., "Reversal of obesity by targeted ablation of adipose tissue," Nature Medicine, Nature Publishing Group, (2004) 10(6): 625-632.

Kythera Biopharmaceuticals: "Evaluation of safety and efficacy of ATX-101 in the reduction of submental fat", 2011, Retrieved from the Internet: URL:http://clinicaltrials.gov/ct2/show/NCT01294644, [retrieved on Feb. 28, 2011].

(56) References Cited

OTHER PUBLICATIONS

Kythera Biopharmaceuticals: "Evaluation of Safety and Efficacy of ATX-101 in the Reduction of Submental Fat", 2011, Retrieved from the Internet: URL:http://clinicaltrials.gov/ct2/show/NCT01305577 [retrieved on Jan. 2, 2015].
Kythera Newsroom. Two Phase 2 studies with ATX-101—study results demonstrated statistically significant reduction in patients' unwanted submental fat. Kythera Biopharmaceuticals, Inc. (2009), 1-2.
Landman B. Beyond Botox. http://newyorkmetro.com/nymetro/health/bestdoctors/cosmeticsurgery/2003/n-.sub.--9281/index.html.
Learn about lecithins. Oxford, CT: American Lecithin Company, 2003.
Lester DS, Baumann D. Action of organic solvents on protein kinase C. Eur J Pharmacol 1991, 206:301-8.
Lichtenberg D, Robson RJ, Dennis EA. Solubilization of phospholipids by detergents. Structural and kinetic aspects. Biochim Biophys Acta 1983, 737:285-304.
Lichtenberg D, Zilberman Y, Greenzaid P, Zamir S. Structural and kinetic studies on the solubilization of lecithin by sodium deoxycholate. Biochemistry 1979, 18:3517-25.
Lichtenberg D. Characterization of the solubilization of lipid bilayers by surfactants. Biochim Biophys Acta 1985, 821:470-8.
Lichtenberg et al., "On the solubility of calcium deoxycholate: kinetics of precipitation and the effect of conjugated bile salts and lecithin," Chem. Phys. Lipids, (1988), 46:279-291.
Lieber CS, Robins SJ, Li J, DeCarli LM, Mak KM, Fasulo JM, Leo MA. Phosphatidylcholine protects againstfibrosis and cirrhosis in the baboon. Gastroenterology 106: 152-9, 1994.
Lipostabil. Rhone-Poulenc Rorer. Cologne, West Germany: Natterman International GMBH, 1990.
Lodish, et al. "Section 3.5—Purifying, Detecting and Characterizing Proteins," Molecular Cell Biology. 4th edition. New York: W. H. Freeman; 2000 pp. 83-99.
MacLachlan I., "Liposomal Formulations for Nucleic Acid Delivery," In Antisense Drug Technology, Principles, Strategies and Applications, 2nd Edition, Crooke S.T.; Ed.; Taylor & Francis Group, (2007), 237-270 ("MacLachlin 2007") at 253.
Mahler et al.,"Protein Aggregation: Pathways, Induction Factors, and Analysis," J. Pharm. Sci., (2009), 98(9):2909-2934.
Martins et al., "Lipid-based colloidal carriers for peptide and protein delivery—liposomes versus lipid nanoparticles," Int. J Nanomedicine, (2007), 2(4):595-607.
McCaslin, "Detergent Properties", Encyclopedia of Biological Chemistry, vol. 1, pp. 577-581 (2004).
Milovic et al. Effects of deoxycholate on human colon cancer cells: apoptosis or proliferation. European Journal of Clinical Investigation. (2002) 32(1):29-34.
Moy, LS. Phosphatidylcholine injections: a study measuring decreased subcutaneous fat thickness. Combined Annual Meeting of the American Society for Dermatologic Surgery and the American Society of Mohs Micrographic Surgery and Cutaneous Oncology, San Diego, CA Sep. 30-Oct. 3, 2004.
Murata et al., "Study of the Micelle Formation of Sodium Deoxycholate. Concentration Dependence of Carbon-13 Nuclear Magnetic Resonance Chemical Shift," J. Phys. Chem., (1982), 86:4690-4694.
Murata et al., "Study on the Micelle Formation of Sodium Deoxycholate, In Solution Behavior of Surfactants," Eds., Mittal K.L. et al., Plenum Press, New York, (1982), 611-627.
Narain, et al.,"Lecithin Protects against Plasma Membrane Disruption by Bile Salts," J. Surg. Res., (1998), 78(2):131-136.
Okuda, et al., "The Organic Composition of Earwax," J. Otolaryngol., (1991), 20(3):212-215.
Parnham MJ, Wendel A. Phospholipids and liposomes—safety for cosmetical and pharmaceutical use. Nattermann Phospholipid GMBH Scientific Publication No. 2 1995.
Powell, A. A. et al. Bile acid hydrophobicity is correlated with induction of apoptosis and/or growth arrest in HCT116 cells. Biochem. J. 2001; 356:481-486.
Rittes, P. G., "The Use of Phosphatidylcholine for Correction of Localized Fat Deposits," Aesth. Plast. Surg. (2003), 27:315-318.
Rittes, P. G., "The use of Phosphatidylcholine for Correction of Lower Lid Bulging Due to Prominent Fat Pads," Dermatol. Surg., (2001), vol. 27:4, pp. 391-392.
Rosenbaum, M., An exploratory investigation of the morphology and biochemistry of cellulite, Annual Meeting of American Society for Aesthetic Surgery, New York, May 1997, 1934-39.
Rossi ABR, Vergnanini AL. Cellulite: a review. JEADV 14:251-62, 2000.
Rotunda A, Suzuki H, Moy RL, Kolodney MS. Detergent effects of sodium deoxycholate are a major feature of injectable phosphatidylcholine. American Society for Dermatologic Surgery, New Orleans, LA, Oct. 11, 2003.
Rotunda et al. "Mesotherapy and Phosphatidylcholine Injections: Historical Clarification and Review" Dermatologic Surgery, (2006) 32: 465-480.
Rotunda et al., "Randomized double-blind clinical trial of subcutaneously injected deoxycholate versus a phosphatidylcholine-deoxycholate combination for the reduction of submental fat", Dermatologic Surgery, 2009, 35(5):792-803.
Rotunda, A.M. et al. Lipomas treated with subcutaneous deoxycholate injections. J. Am. Acad. Dermatol. 2005; 53(6): 973-978.
Rotunda, et al. "Detergent Effects of Sodium Deoxycholate Are a Major Feature of an Injectable Phosphatidylcholine Formulation Used for Localized Fat Dissolution" Dermatologic Surgery, 2004, vol. 30, pp. 1001-1008.
Ryden et al., "The effects of pH and bile salts on the binding of MeIQx to wheat bran fibre," Mutation Res., (1996), 351:45-52.
Sachs et al., "The Effect of Pyrophosphate on the Amino Acid Incorporating System of Rat Liver Microsomes," J. Biol. Chem., (1958), 233(3):650-656.
Sager S. New fat removal technique getting raves: Is it safe? Does it work? http://abclocal.go.com/wabc/news/wabc.sub.--020703.sub.--mesotherap- y.html, Feb. 7, 2003.
Salti, et al., "Phosphatidylcholine and Sodium Deoxycholate in the Treatment of Localized Fat: A Double-Blind, Randomized Study," Dermatol Surg., (2008), 34:60-66.
Schuck S, Honsho M, Ekroos K, Shevchenko A, Simons K. Resistance of cell membranes to different detergents. Proc Natl Acad Sci 2003, 100:5795-800.
Sergio, M. Traitement mesotherapique des xanthelasmas a la phophatidilcoline polyinsaturee (EPL). V Congres Internacional de Mesotherapie, Paris: Dermatologie, 1988; 364.
Serra M., Subcutaneous infiltration with phosphatidylcholine solution for treatment of buffalo hump and fatty pads. 3rd Int'l workshop on adverse drug reactions and lipodystrophy in HIV, Athens, Oct. 2001, 115.
Shimazawa et al., "Involvement of ER stress in retinal cell death", Mol Vis, 2007, 13:578-587.
Sigma Product Information Sheet, Sodium deoxycholate,Product No. D6750, May 2006.
SIGMA: "RIPA Buffer", Product No. R0278, Sep. 2003, retrieved from the internet: URL:http://www.sigmaaldrich.com/etc/medialib/docs/Sigma/Bulletin/r0278bul.Par.0001.File.tmp/r0278bul.pdf.
Singer SJ, Nicolson GL. The fluid mosaic model of the structure of cell membranes. Science 1972, 175:720-31.
Small, "Size and Structure of Bile Salt Micelles. Influence of Structure, Concentration, Counterion Concentration, pH, and Temperature", In Molecular Association in Biological and Related Systems; Goddard, E.; Advances in Chemistry; American Chemical Society: Washington, DC, Chapter 4; pp. 31-52, 1968.
Smith, S. , "A Heated Debate on Hot Shot Fat-Zapper," The New York Post, Dec. 8, 2002, 12.
Stavroudis C., "Sorting Out Surfactants," WAAC Newsletter, (2009), 31(1):18-21.
Stoll et al., "In Vitro Dissolution and In Vivo Absorption of Nitrofurantoin from Deoxycholic Acid Coprecipitates," J Pharm. Sci., (1973), 62(1):65-68.
Su et al., "Regulation of System A Amino Acid Transport in 3T3-L1 Adipocytes by Insulin." J. Biol. Chem., (1998), 273(6):3173-3179.

(56) References Cited

OTHER PUBLICATIONS

Teelmann K, Schlappi B, Schupbach M, Kistler A. Preclinical safety evaluation of intravenously administered mixed micelles. Arzneimittelforschung 1984,34:1517-23.

Toyama M. Next-Gen Liposuction. http://www.time.com/time/europe/forecast2003/html/liposuction.html, Dec. 8, 2002.

U.S. Non-Final Office Action on U.S. Appl. No. 14/175,086 dated Sep. 30, 2016.

U.S. Notice of Allowance dated Apr. 7, 2017 in U.S. Appl. No. 14/175,086.

U.S. Notice of Allowance dated Oct. 4, 2012 in U.S. Appl. No. 13/323,605.

U.S. Notice of Allowance on U.S. Appl. No. 15/650,556 dated May 18, 2018.

U.S. Office Action dated May 12, 2011 in U.S. Appl. No. 12/716,070.

U.S. Office Action dated Feb. 1, 2016 in U.S. Appl. No. 14/175,086.

U.S. Office Action dated Jul. 20, 2012 in U.S. Appl. No. 13/323,605.

U.S. Office Action from U.S. Appl. No. 13/733,729, dated Nov. 18, 2014.

U.S. Office Action from U.S. Appl. No. 14/175,086 dated Jun. 18, 2015.

Victor S. Phosphatidylcholine works. Skin and Allergy News 2003, 34.

Wendel, A., Lecithin: The First 150 Years—Part II: Evolution to a global pharmaceutical industry, Inform, (2000), 11:992-997.

Womack et al., "Detergent Effects on Enzyme Activity and Solubilization of Lipid Bilayer Membranes", Biochimica et Biophysica Acta, 733, pp. 210-215 (1983).

Wright et al., "Formulation Development of AAV2 Vectors: Identification of Excipients That Inhibit Vector Aggregation," Mo. Therapy, (2004), 9(Supplement 1):S163, Abstract 425.

Young, VL. Lipostabil: The effect of phosphatidylcholine on subcutaneous fat. Aesthetic Surg J 23:413-417,2003.

Zeghari et al., "Adipocyte and erythrocyte plasma membrane phospholipid composition and hyperinsulinemia: a study in nondiabetic and diabetic obese women", International Journal of Obesity and Related Metabolic Disorders:Journal of the International Association for the Study of Obesity, 2000, 24(12):1600-1607.

Zhang et al., "A potent small molecule inhibits polyglutamine aggregation in Huntington's disease neurons and suppresses neurodegeneration in vivo," Proc. Natl. Acad. Sci., (2005), 102(3):892-897.

FORMULATIONS OF DEOXYCHOLIC ACID AND SALTS THEREOF

CROSS-REFERENCE TO RELATED APPLICATIONS

This application is a continuation of U.S. patent application Ser. No. 15/650,556, filed Jul. 14, 2017, which is a continuation of U.S. patent application Ser. No. 14/175,086, filed Feb. 7, 2014, which is a continuation of U.S. patent application Ser. No. 13/733,729, filed Jan. 3, 2013, now U.S. Pat. No. 9,186,364, which is a continuation of U.S. patent application Ser. No. 13/323,605, filed Dec. 12, 2011, now U.S. Pat. No. 8,367,649, which is a continuation of U.S. patent application Ser. No. 12/716,070, filed Mar. 2, 2010, now U.S. Pat. No. 8,101,593, which claims the benefit under 35 U.S.C. § 119(e) to U.S. Provisional Patent Application No. 61/274,129, which was converted from U.S. patent application Ser. No. 12/397,229, filed Mar. 3, 2009, all of which are hereby incorporated by reference herein in their entireties.

FIELD

The present invention relates to pharmaceutical formulations of acid in water wherein the formulation is maintained at a pH such that precipitation of sodium deoxycholate is substantially inhibited.

BACKGROUND

Rapid removal of body fat is an age-old ideal, and many substances have been claimed to accomplish such results, although few have shown results. "Mesotherapy," or the use of injectables for the removal of fat, is not widely accepted among medical practitioners due to safety and efficacy concerns, although homeopathic and cosmetic claims have been made since the 1950's. Mesotherapy was originally conceived in Europe as a method of utilizing cutaneous injections containing a mixture of compounds for the treatment of local medical and cosmetic conditions. Although mesotherapy was traditionally employed for pain relief, its cosmetic applications, particularly fat and cellulite removal, have recently received attention in the United States. One such reported treatment for localized fat reduction, which was popularized in Brazil and uses injections of phosphatidylcholine, has been erroneously considered synonymous with mesotherapy. Despite its attraction as a purported "fat-dissolving" injection, the safety and efficacy of these cosmetic treatments remain ambiguous to most patients and physicians (see, Rotunda, A. M. and M. Kolodney, Dermatologic Surgery "Mesotherapy and Phosphatidylcholine Injections: Historical Clarification and Review", 2006, 32: 465-480).

Recently published literature reports that the bile acid deoxycholic acid has fat removing properties when injected into fatty deposits in vivo (See, WO 2005/117900 and WO 2005/112942, US2005/0261258; US2005/0267080; US2006/127468; and US2006/0154906). Deoxycholate injected into fat tissue has the effects of: 1) degrading fat cells via a cytolytic mechanism; and 2) causing skin tightening. Both of these effects are required to mediate the desired aesthetic corrections (i.e., body contouring). The effects of deoxycholate into fat are spatially contained because deoxycholate injected into fat is rapidly inactivated by exposure to protein, e.g. albumin, and then rapidly returns to the intestinal contents. As a result of this attenuation effect that confers clinical safety, fat removal therapies typically require 4-6 sessions. This localized fat removal without the need for surgery is beneficial not only for therapeutic treatment relating to pathological localized fat deposits (e.g., dyslipidemias incident to medical intervention in the treatment of HIV), but also for cosmetic fat removal without the attendant risk inherent in surgery (e.g., liposuction) (see, Rotunda et al., Dermatol. Surgery "Detergent effects of sodium deoxycholate are a major feature of an injectable phosphatidylcholine formulation used for localized fat dissolution", 2004, 30: 1001-1008; and Rotunda et al., J. Am. Acad. Dermatol. "Lipomas treated with subcutaneous deoxycholate injections", 2005: 973-978).

All publications and patent applications mentioned in this specification are herein incorporated by reference to the same extent as if each individual publication or patent application was specifically and individually indicated to be incorporated by reference.

SUMMARY

It has been found that aqueous solutions of sodium deoxycholate at low (i.e., <5% w/v) concentrations of sodium deoxycholate can be stabilized by adjusting the pH of the solution. The present invention is directed to an aqueous pharmaceutical formulation comprising less than about 5% w/v sodium deoxycholate wherein the formulation is maintained at a pH sufficient to substantially inhibit precipitation of the sodium deoxycholate.

Also disclosed herein, are methods for inhibiting precipitation of sodium deoxycholate in an aqueous solution comprising less than about 5% w/v of sodium deoxycholate, said method comprising maintaining pH of the solution from about 8.0 to about 8.5.

BRIEF DESCRIPTION OF THE DRAWINGS

(FIGS. 1A, 1B and 1C) and 25° C. (FIGS. 1D, 1E and 1F).

FIG. 2A is a comparison of the 5 mg (0.5% w/v) samples tested in FIGS. 1A, 1B, 1C, 1D, 1E and 1F. FIG. 2B is a comparison of the 50 mg (5% w/v) samples tested in FIGS. 1A, 1B, 1C, 1D, 1E and 1F. FIG. 2C is a comparison of the 100 mg (10% w/v) samples tested in FIGS. 1A, 1B, 1C, 1D, 1E and 1F. FIG. 2D is a comparison of the 160 mg (16% w/v) samples tested in FIGS. 1A, 1B, 1C, 1D, 1E and 1F.

DETAILED DESCRIPTION

Figure 1A:
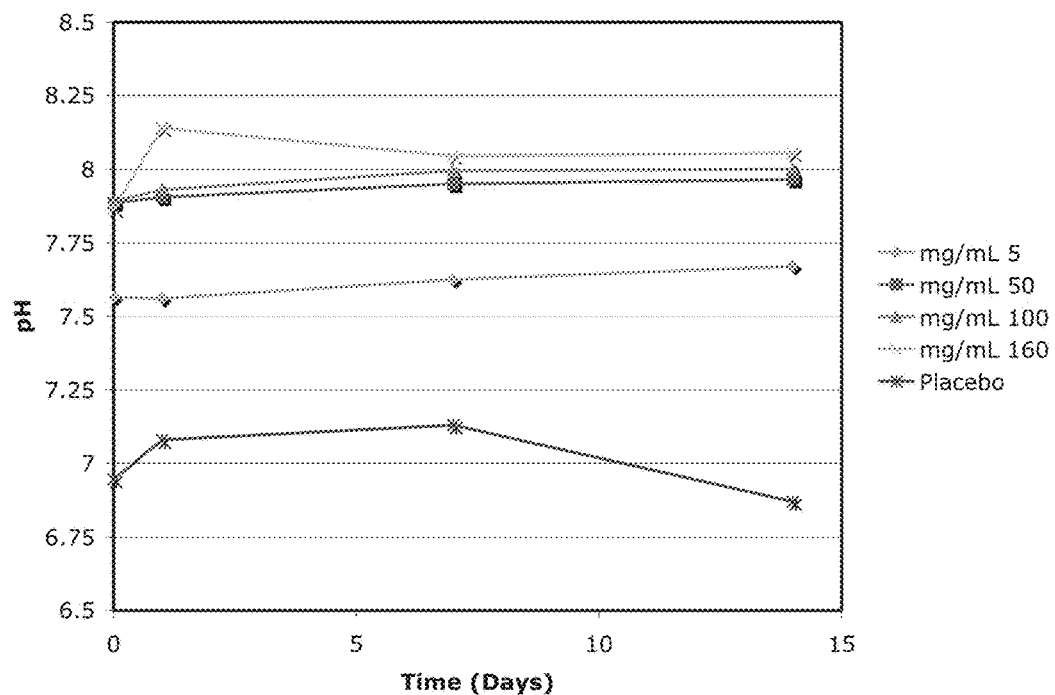
FIGS. 1A, 1B, 1C, 1D, 1E and 1F show the variability in pH over a two week period of formulations containing 5, 50, 100 and 160 mg/mL (0.5, 5, 10 and 16% w/v) sodium deoxycholate at 4° C.
Figure 1B:
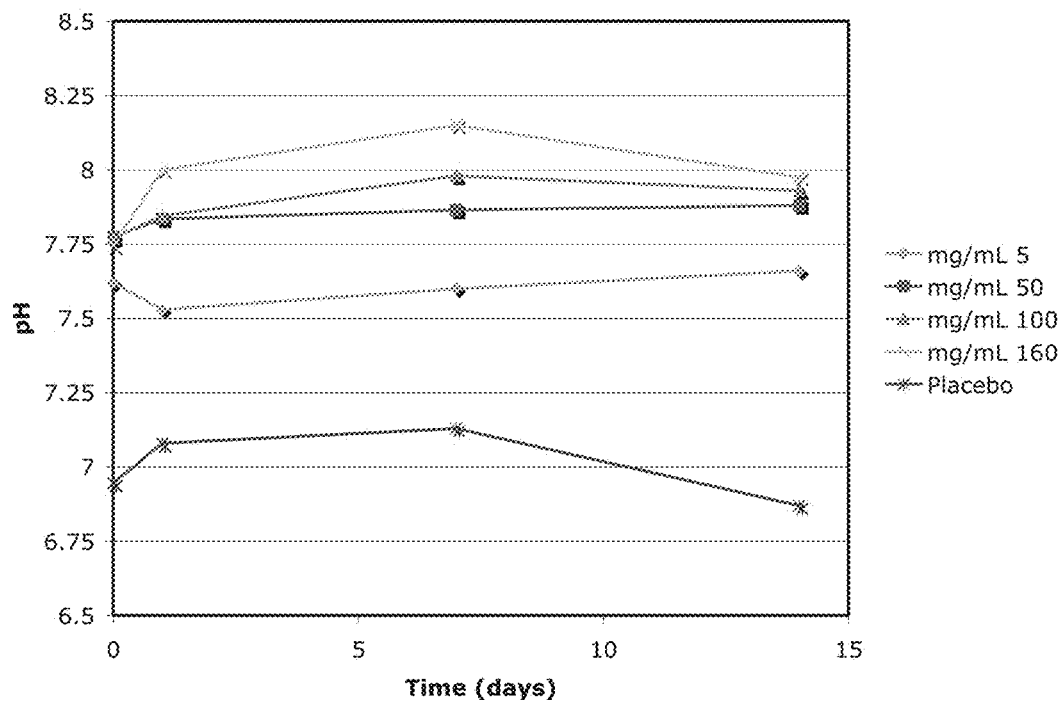
Figure 1C:
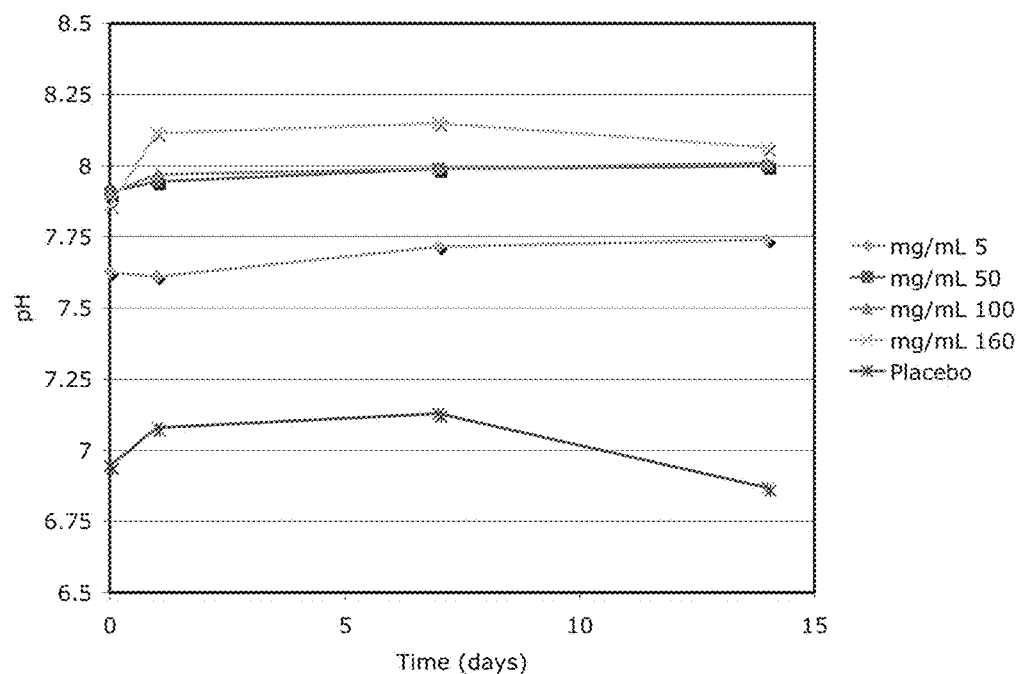
Figure 1D:
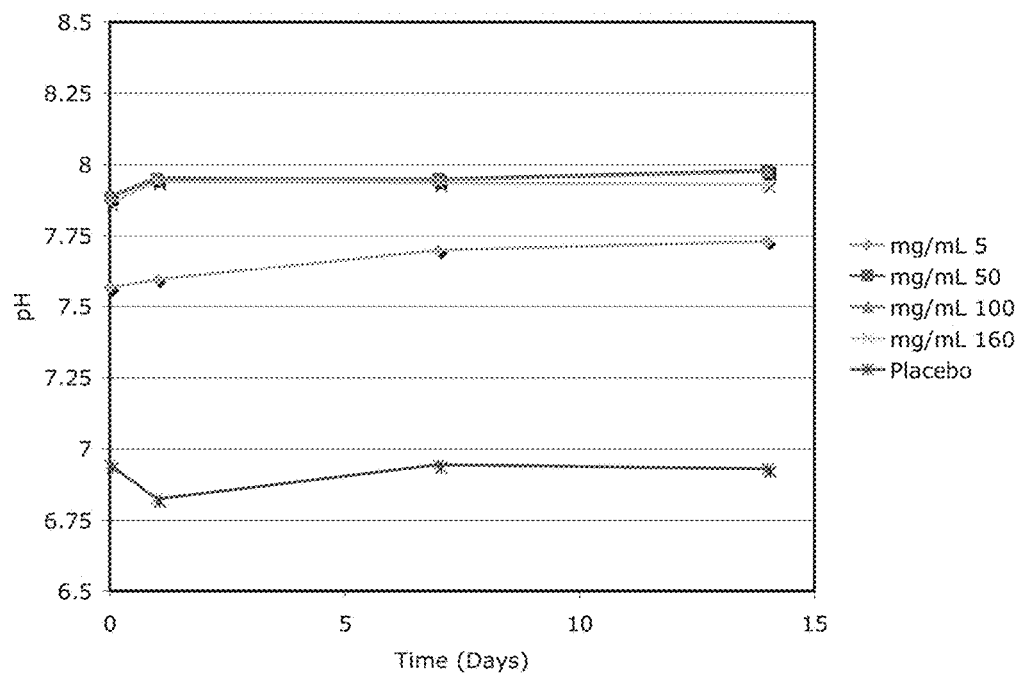
Figure 1E:
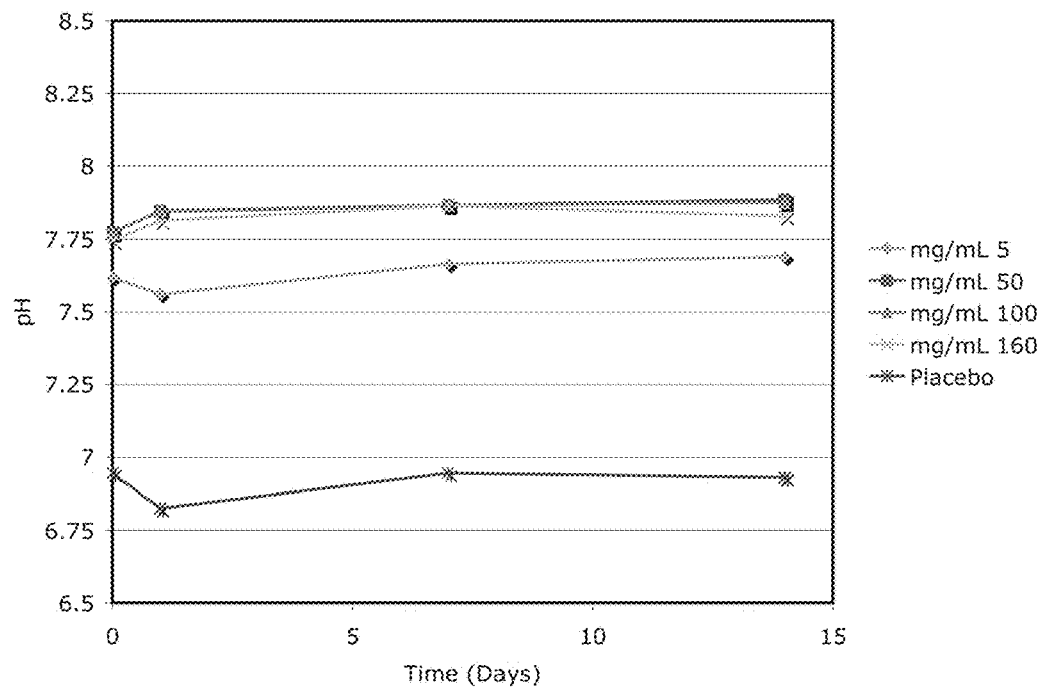
Figure 1F:
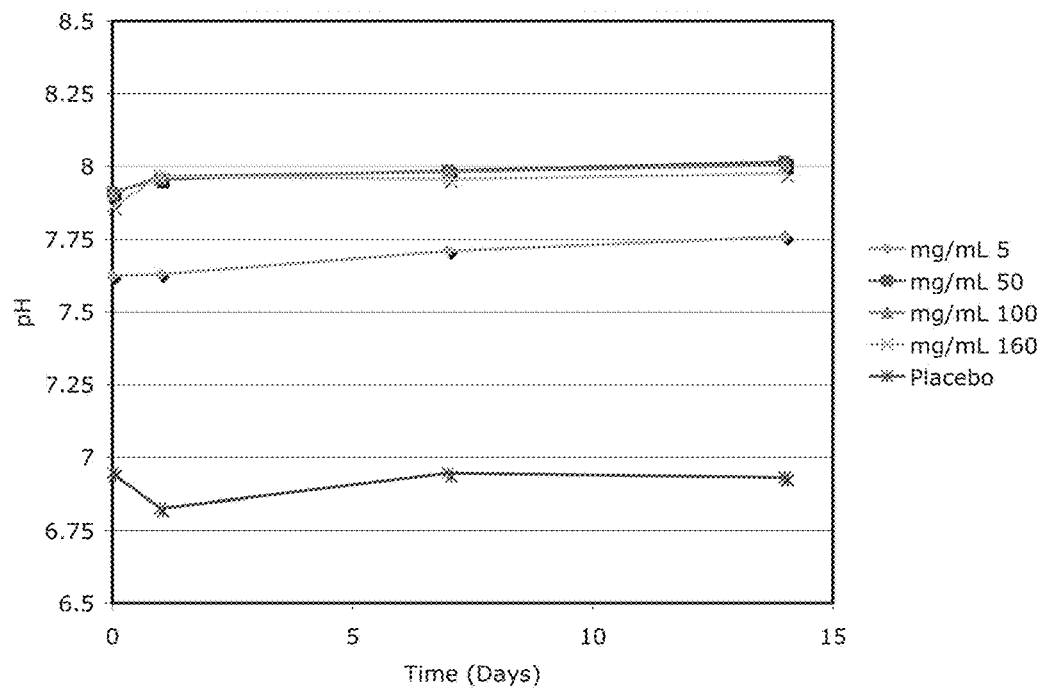
Figure 2A:
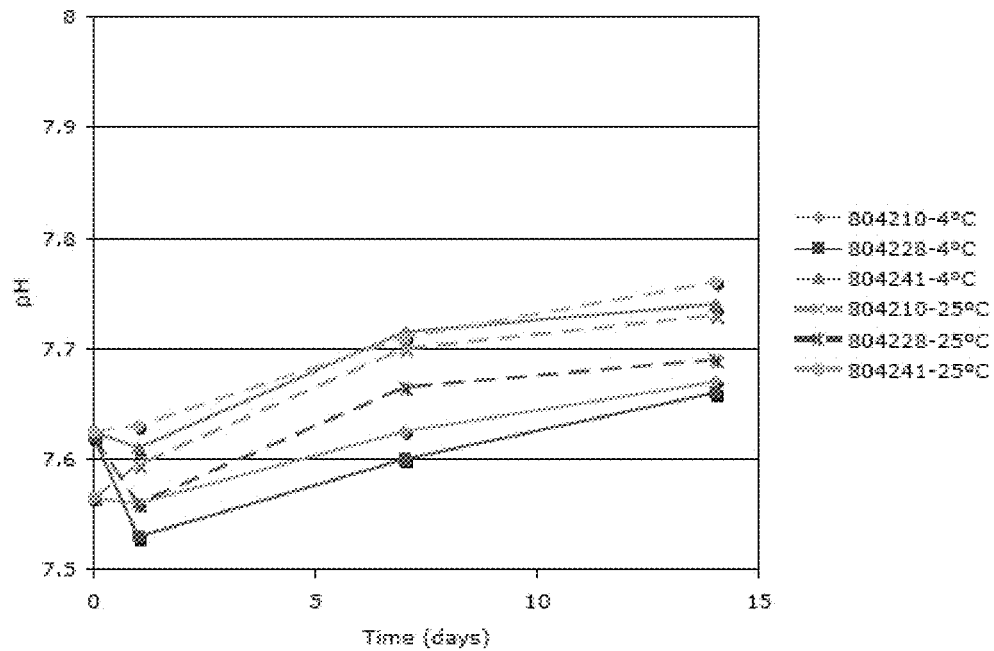
FIGS. 2A, 2B, 2C and 2D show that solubility is independent of lot to lot variability in pH.
Figure 2B:
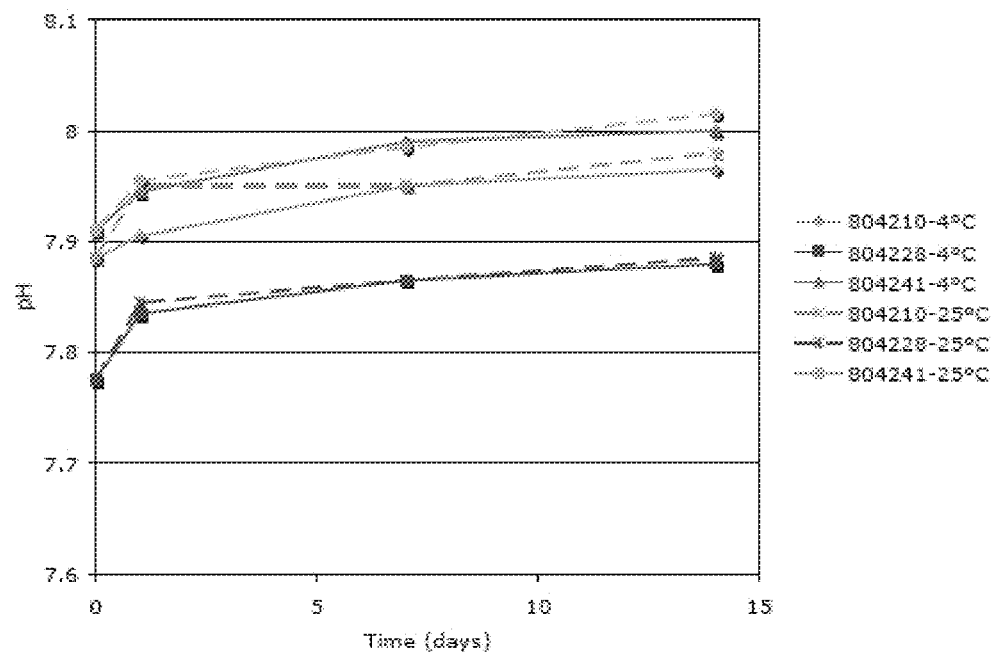
Figure 2C:
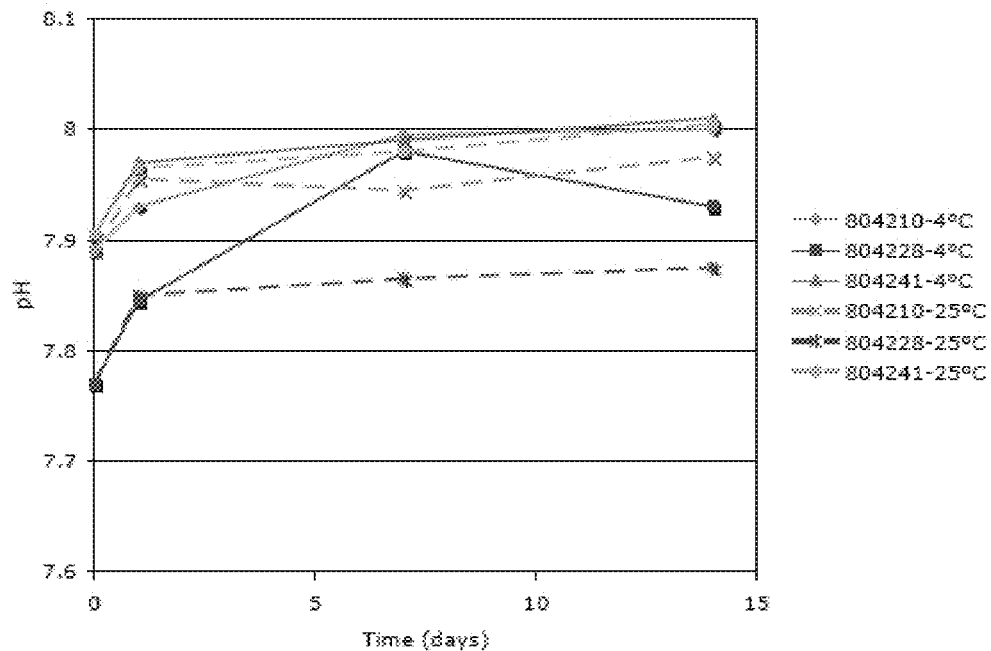
Figure 2D:
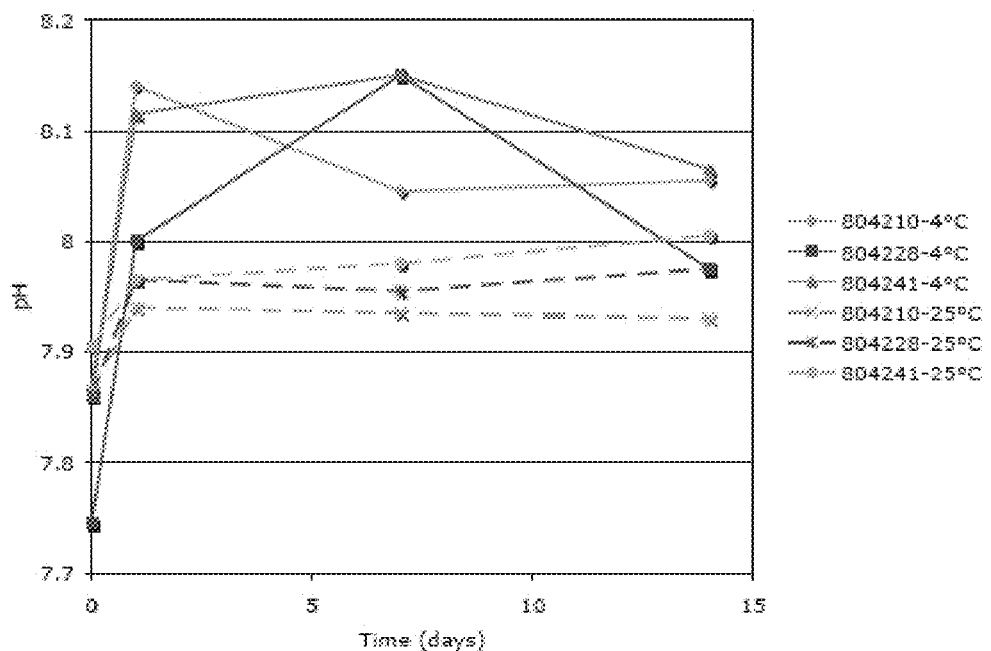

As used herein, certain terms have the following defined meanings.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

As used herein, the term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used herein, the term "sodium deoxycholate" refers to sodium (4R)-4-((3R,5R,10S,12S,13R,17R)-3,12-dihydroxy-10,13-dimethylhexadecahydro-1H-cyclopenta[a]phenanthren-17-yl)pentanoate as shown below. Other stereoisomers are within the scope of the invention.

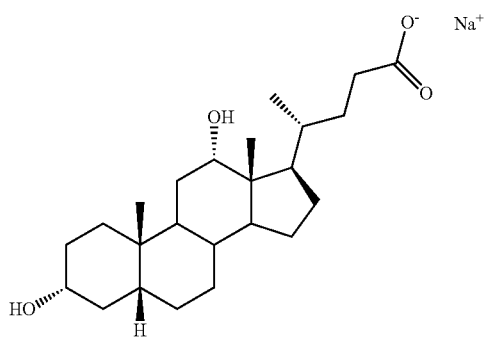

Sodium deoxycholate or sodium (4R)-4-((3R,5R,10S,12S,13R,17R)-3,12-dihydroxy-10,13-dimethylhexadecahydro-1H-cyclopenta[a]phenanthren-17-yl)pentanoate can be prepared according to the methods disclosed in U.S. Patent Publication No. 2008/0318870A1 entitled "Synthetic Bile Acid Composition, Method And Preparation" filed on Feb. 21, 2008, which is hereby incorporated by reference in its entirety.

As used herein, the term "aqueous pharmaceutical formulation" refers to a formulation of sodium deoxycholate in water suitable for administration to a patient.

As used herein, the term "buffer" refers to an aqueous solution comprising a mixture of a weak acid and its conjugate base or a weak base and its conjugate acid. A buffer has the property that the pH of the solution changes very little when a small amount of acid or base is added to it. Buffer solutions are used as a means of keeping pH at a nearly constant value in a wide variety of chemical applications. Examples of suitable buffers include phosphate buffers and those known in the literature (see, for example, Troy, D. B., ed. (2005) Remington: The Science and Practice of Pharmacy, 21$^{st}$ ed., Lippincott Williams & Wilkins).

As used herein, the term "base" refers to various typically water-soluble compounds, molecules or ions that in solution have a pH greater than 7. Such compounds, molecules or ions are able to take up a proton from an acid or are able to give up an unshared pair of electrons to an acid. Examples of suitable bases include metal carbonates and bicarbonates, for example sodium carbonate, calcium carbonate, magnesium carbonate, zinc carbonate, sodium bicarbonate and the like; and metal hydroxides, for example sodium hydroxide, potassium hydroxide, and the like, such as those known in the literature (see, for example, Troy, D. B., ed. (2005) Remington: The Science and Practice of Pharmacy, 21$^{st}$ ed., Lippincott Williams & Wilkins).

As used herein, the term "metal carbonates" refers to the metal salt of $CO_3^{2-}$. For example, sodium carbonate, calcium carbonate, magnesium carbonate, zinc carbonate, and the like.

As used herein, the term "metal bicarbonates" refers to the metal salt of $HCO_3^-$. For example, sodium bicarbonate, and the like.

As used herein, the term "metal hydroxides" refers to the metal salt of $^-OH$. For example, sodium hydroxide, potassium hydroxide, and the like.

As used herein, the terms "sterile water" or "water for injection" refer to a sterile, nonpyrogenic preparation of water for injection which contains no bacteriostat, antimicrobial agent or added buffer. In general, the osmolar concentration of additives totals at least 112 mOsmol/liter (two-fifths of the normal osmolarity of the extracellular fluid ~280 mOsmol/liter).

As used herein, the term "benzyl alcohol" refers to the compound

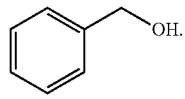

As used herein, the term "precipitation" refers to the formation of a solid in a solution. As used herein, the term "solution" refers to a substantially homogeneous mixture comprising two or more substances dissolved in a solvent.

As used herein, the term "substantially inhibit precipitation" means to inhibit most or all visible precipitation or maintain homogeneity. This may be done over a desired period of time.

As used herein, the term "relative standard deviation for homogeneity" or "$H_E$" refers to the value obtained by dividing the standard deviation of the homogeneity by the absolute value of the mean. An $H_E$ less than 10 indicates very good homogeneity.

Formulations

Knowledge about the chemical and physical stability of a drug formulation in the desired media for delivery is valuable. In the longer term, the stability of the formulation will dictate the shelf life of the marketed product. It is preferable that the active ingredient in a pharmaceutical formulation be at the required concentration when administered to a patient.

Current methods for the administration of sodium deoxycholate to a patient include the administration of a low concentration (i.e., <5% w/v) of an aqueous solution of sodium deoxycholate, as it has been shown that the low concentration is beneficial for the effective and safe removal of fat deposits in the body. However, it has been observed that a precipitate forms at both relatively low (i.e., <5% w/v) and high (i.e., >16% w/v) concentrations of sodium deoxycholate in aqueous media. This precipitation results in a limited shelf life of aqueous solutions of sodium deoxycholate, even at cold temperatures (3-5° C.). This instability of aqueous solutions of sodium deoxycholate can be circumvented by the preparation of an aqueous solution of sodium deoxycholate at a concentration of about 5% to about 16% w/v, and having the practitioner dilute the pharmaceutical composition of sodium deoxycholate just prior to use. Whereas this dilution method is effective to allow for both storage stability and effective patient dosing, it is not ideal as a method for routine use.

It has been found that aqueous solutions of sodium deoxycholate at low (i.e., <5% w/v) concentrations of sodium deoxycholate can be stabilized adjusting the pH of the solution. The present application is directed to an aqueous pharmaceutical formulation comprising less than about 5% w/v sodium deoxycholate wherein the formulation is maintained at a pH sufficient to substantially inhibit precipitation of the sodium deoxycholate. In some embodiments, the pharmaceutical formulation, comprising less than about 5% w/v sodium deoxycholate in water, or alternatively, less than about 4.5%, or alternatively, less than about 4%, or alternatively, less than about 3.5%, or alternatively, less than about 3%, or alternatively, less than about 2.5%, or alternatively, less than about 2%, or alternatively, less than about 1.5%, or alternatively, less than about 1%, or alternatively, less than about 0.75%, or alternatively, less than about 0.5%, or alternatively, less than about 0.1% w/v sodium deoxycholate in water.

Sodium deoxycholate or sodium (4R)-4-((3R,5R,10S,12S,13R,17R)-3,12-dihydroxy-10,13-dimethylhexadecahydro-1H-cyclopenta[a]phenanthren-17-yl)pentanoate can be prepared according to the methods disclosed in U.S. Patent Publication No. 2008/0318870A1 entitled "Synthetic Bile Acid Composition, Method And Preparation" filed on Feb. 21, 2008, which is hereby incorporated by reference in its entirety.

In one embodiment, the pharmaceutical formulations disclosed herein are suitable for injection into a human. The method of injection can be any type of injection, such as subcutaneous injection, as well as other forms of injection. Therefore, in some embodiments, the aqueous formulation is sterile. The aqueous formulation can be prepared using sterile water or water for injection (WFI).

In one aspect of the present invention, the precipitation of sodium deoxycholate is substantially inhibited for a period of at least about six months. In another aspect, the precipitation of sodium deoxycholate is substantially inhibited for a period of at least about one year. In yet another aspect, the precipitation of sodium deoxycholate is substantially inhibited for a period of at least about two years.

It is contemplated that when stored at various temperatures, for example at ambient or cold temperatures, the formulation can have an increased shelf life. In certain embodiments, the formulation is stored at a temperature of from about 17° C. to about 27° C. In some embodiments, the temperature of the formulation is increased to a temperature of about 25° C. to about 37° C. In other embodiments, the formulation is stored at a temperature of from about 2° C. to about 8° C.

In certain embodiments, the pH of the formulation ranges from about 8.0 to about 8.5. In one embodiment, the pH of the formulation is about 8.0, or alternatively, about 8.1, or alternatively, about 8.2, or alternatively, about 8.3, or alternatively, about 8.4, or alternatively, about 8.5.

In one embodiment, the pH is established by the use of a base. It is contemplated that any base can be used to increase the pH of the formulation provided that it does not react with the sodium deoxycholate and will not cause harm to the patient. In some embodiments, the base is selected from the group consisting of metal carbonates, metal bicarbonates, metal hydroxides, or a mixture thereof. Examples of bases include, but are not limited to, a base selected from the group consisting of sodium carbonate, calcium carbonate, magnesium carbonate, zinc carbonate, sodium bicarbonate, sodium hydroxide and potassium hydroxide or a mixture thereof. In one embodiment, the base is sodium hydroxide.

In certain cases, the pH of the formulation may be maintained with the use of a buffer. Various buffers are known in the art and it is contemplated that any buffer having buffering capacity at the desired pH can be used in the formulations disclosed herein. In one embodiment, the buffer is a phosphate buffer. The amount of phosphate in the formulation can be determined to provide a desired pH and salt concentration. In one embodiment, the formulation comprises about 10 mM phosphate.

In some embodiments, the formulation comprises at least one excipient to aid in achieving a formulation with desired properties, such as increased solubility, preservability or to provide an isotonic solution. Such excipients are known in the art. In one embodiment, the formulation comprises about 1% sodium chloride. In another embodiment, the formulation comprises about 1% benzyl alcohol. In some embodiments, the formulation comprises about 1% benzyl alcohol and about 1% sodium chloride. In some embodiments, the formulation comprises about 0.9% benzyl alcohol and about 0.9% sodium chloride.

The formulations disclosed herein comprise less than about 5% w/v sodium deoxycholate in water maintained at a pH sufficient to substantially inhibit precipitation of the sodium deoxycholate. The amount of precipitation or homogeneity of the formulation can be measured using various methods. For example, it can be measured quantitatively using light scattering by illuminating the formulation with a spectrophotometer. Or alternatively, the homogeneity can be measured qualitatively by observing the visual clarity of the solution with the eye. In some embodiments, the formulation has a relative standard deviation for homogeneity of less than about 5%. Alternatively, the formulation has a relative standard deviation for homogeneity of less than about 4%, or alternatively, about 3%, or alternatively, about 2%, or alternatively, about 1%.

The use of prodrugs of sodium deoxycholate in the formulations disclosed herein are also contemplated. A prodrug is an active or inactive compound that is modified chemically through in vivo physiological action, such as hydrolysis, metabolism and the like, into a compound of the embodiments following administration of the prodrug to a patient. For example, one may prepare an ester of the present deoxycholic acid at either or both of the hydroxyl groups thereon or of suitable derivatives thereof, so that the release of the deoxycholic acid or derivatives thereof is triggered by the disruption of the cell membrane, and release of esterase.

With the release of esterase, the ester protecting group is cleaved so that the deoxycholic acid active form or derivatives thereof is present at the desired location in situ. For a general discussion of prodrugs involving esters see Svensson and Tunek Drug Metabolism Reviews 165 (1988) and Bundgaard Design of Prodrugs, Elsevier (1985).

In some embodiments, the solutions herein do not include lipids, phospholipids, or phosphatidylcholine. In some embodiments, the solutions herein include up to 5% w/w, w/v, or v/v lipids, specifically phospholipids, or more specifically phosphatidylcholine.

In some embodiments, the aqueous pharmaceutical formulation of the invention can further comprise a second therapeutic agent selected from the group consisting of: anti-microbial agents, vasoconstrictors, anti-thrombotic agents, anti-coagulation agents, suds-depressants, anti-inflammatory agents, analgesics, dispersion agents, anti-dispersion agents, penetration enhancers, steroids, tranquilizers, muscle relaxants, and anti-diarrhea agents. In some embodiments, a solution is in a container that contains up to 500 mL of solution. Such container can be a syringe or syringe-loadable container.

In some embodiments, the formulations further comprise a molecule known to cause fat to die by an orthogonal mechanism. Such molecules include neuropeptide Y (NPY) antagonists including, but not limited to, NPY receptor antagonists, such as BIBP-3226 (Amgen), MO-3304 (Boehringer Ingleheim), BMS-192548 and AR-H040922 (Bristol-Myers Squibb), LY-357897 (Eli Lilly), 1229U91 and GW4380145 (GlaxoSmithKline), JNJ-5207787 (Johnson & Johnson), Lu-AA-44608 (Lundbeck), MK-0557 (Merck NPY), NGD-95-1 (Neurgogen), NLX-E201 (Neurologix), CGP-71683 (Novartis), PD-160170 (Pfizer), SR-120819A, BIIE0246, and S.A.0204 (Sanofi Aventis), S-2367 (Shiongli), dihydropyridine and dihydropyridine derivatives that are NPY receptor antagonists, bicyclic compounds that are NPY receptor antagonists, carbazole NPY receptor antagonists, and tricyclic compounds that are NPY receptor antagonists (See, e.g., WO 2006/133160 and U.S. Pat. No. 6,313,128). Also contemplated are fat selective pro-apoptotic peptides such as the CKGGRAKDC peptide that homes to white fat vasculature (See, Kolonin M. G. et al., Nat. Med., 2004, 10(6): 625-32).

Another aspect of the invention relates to mixing adipoablative bile acids, such as, deoxycholic acid (DCA) with agents that kill fat cells. In one aspect, this invention contemplates a means to enhance the aesthetic effects of deoxycholate injections by mixing into the deoxycholate injectate a molecule that causes fat to die by an orthogonal mechanism. Examples of such candidate molecules include, but are not limited to, neuropeptide Y (NPY) antagonists and fat selective pro-apoptotic peptides. Since both fat cell killing and skin tightening may be required to mediate the desired effects, the effects of an agent with fat killing ability and potent skin tightening effects (such as deoxycholate) can be enhanced via the addition of a molecule with potent fat cell killing effects. Additionally, molecules that require access to the vasculature to kill (such as certain pro-apoptotic peptides that bind to proteins expressed on the luminal side of capillaries) can gain access to these proteins because deoxycholate may cause vascular leakage. Thus, such agents can be synergistic with deoxycholate potentially creating a more potent means to mediate body contouring in fewer therapeutic sessions.

Examples of NPY antagonists include, but are not limited to, NPY receptor antagonists, such as BIBP-3226 (Amgen), BIBO-3304 (Boehringer Ingleheim), BMS-192548 and AR-H040922 (Bristol-Myers Squibb), LY-357897 (Eli Lilly), 1229U91 and GW4380145 (GlaxoSmithKline), JNJ-5207787 (Johnson & Johnson), Lu-AA-44608 (Lundbeck), MK-0557 (Merck NPY), NGD-95-1 (Neurgogen), NLX-E201 (Neurologix), CGP-71683 (Novartis), PD-160170 (Pfizer), SR-120819A, BIIE0246, and S.A.0204 (Sanofi Aventis), S-2367 (Shiongli), dihydropyridine and dihydropyridine derivatives that are NPY receptor antagonists, bicyclic compounds that are NPY receptor antagonists, carbazole NPY receptor antagonists, and tricyclic compounds that are NPY receptor antagonists. See, e.g., WO 2006/133160 and U.S. Pat. No. 6,313,128 (incorporated herein by reference in its entirety including figures).

Exemplary fat selective pro-apoptotic peptides includes, but is not limited to, CKGGRAKDC peptide that homes to white fat vasculature. See, Kolonin M. G. et al., Nat. Med. June 10(6):625-32 (2004).

Sodium deoxycholate or sodium (4R)-4-((3R,5R,10S, 12S,13R,17R)-3,12-dihydroxy-10,13-dimethylhexadecahydro-1H-cyclopenta[a]phenanthren-17-yl)pentanoate can be prepared according to the methods disclosed in U.S. Patent Publication No. 2008/0318870A1 entitled "Synthetic Bile Acid Composition, Method And Preparation" filed on Feb. 21, 2008, which is hereby incorporated by reference in its entirety. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Methods

Disclosed herein is a method for inhibiting precipitation of sodium deoxycholate in an aqueous solution comprising less than about 5% w/v of sodium deoxycholate, said method comprising maintaining pH of the solution from at least about 8.0 to about 8.5.

In one aspect of the present invention, methods disclosed herein substantially inhibit the precipitation of sodium deoxycholate in solution over a period of at least about six months. In another aspect, the precipitation of sodium deoxycholate is substantially inhibited for a period of at least about one year. In yet another aspect, the precipitation of sodium deoxycholate is substantially inhibited for a period of at least about two years.

It has been found that the pH of the solution can inhibit the precipitation of sodium deoxycholate at concentrations of less than about 5% w/v in water allow the sodium deoxycholate to be maintained in solution. In one embodiment, the pH is established by the use of a base. It is contemplated that any base can be used to increase the pH of the formulation provided that it does not react with the sodium deoxycholate. In some embodiments, the base is selected from the group consisting of metal carbonates, metal bicarbonates, and metal hydroxides, or a mixture thereof. Examples of bases include, but are not limited to, a base selected from the group consisting of sodium carbonate, calcium carbonate, magnesium carbonate, zinc carbonate, sodium bicarbonate, sodium hydroxide and potassium hydroxide or a mixture thereof. In one embodiment, the base is sodium hydroxide.

In certain embodiments, the pH ranges from about 8.0 to about 8.5. In one embodiment, the pH of the formulation is about 8.0, or alternatively, about 8.1, or alternatively, about 8.2, or alternatively, about 8.3, or alternatively, about 8.4, or alternatively, about 8.5. In one embodiment, the pH of the aqueous solution is about 8.3.

In certain cases, the pH of the formulation may need to be maintained with the use of a buffer. Various buffers are know in the art and it is contemplated that any buffer having buffering capacity at the desired pH can be used in the formulations disclosed herein. In one embodiment, the buffer is a phosphate buffer. The amount of phosphate required to provide a desired pH and salt concentration can be calculated using methods well known in the art. In one embodiment, the formulation comprises about 10 mM phosphate.

In one embodiment, the methods disclosed herein provide formulations which are suitable for injection into a human. The method of injection can be any type of injection, such as subcutaneous injection, as well as other forms of injection. Therefore, in some embodiments, the aqueous solution comprises sterile water or water for injection (WFI).

In one aspect, it may be that one or more excipients are used to maintain the solubility, or increase the preservability of sodium deoxycholate present in the formulation. In one embodiment, the method comprises adding about 1% benzyl alcohol. In some embodiments, the formulation also comprises at least one excipient to aid in achieving an isotonic solution. Such excipients are known in the art. In one embodiment, the method comprises adding about 1% sodium chloride. In some embodiments, the method comprises adding both 1% benzyl alcohol and 1% sodium chloride. In some embodiments, the method comprises adding both 0.9% benzyl alcohol and 0.9% sodium chloride. Using the methods disclosed herein, an aqueous solution comprising less than about 5% w/v sodium deoxycholate is maintained at a pH sufficient to substantially inhibit precipitation of the sodium deoxycholate. The amount of precipitation or homogeneity of the formulation can be measured using various methods. For example, it can be measured quantitatively by measuring the light scattering via illumination by a spectrophotometer. Or alternatively, the homogeneity can be measured qualitatively by simply observing the visual clarity of the solution with the eye. In some embodiments, the method provides a pharmaceutical formulation having a relative standard deviation for homogeneity of less than about 5%. Alternatively, the relative standard deviation for homogeneity of less than about 4%, or alternatively, about 3%, or alternatively, about 2%, or alternatively, about 1%.

The storage temperature can assist in maintaining the solubility of the sodium deoxycholate of the formulation. In certain embodiments, the storage temperature is from about 17° C. to about 27° C. In some embodiments, the storage temperature is about 25° C. to about 37° C. In other embodiments, the storage temperature is from about 2° C. to about 8° C.

It is contemplated that the sodium deoxycholate concentration can vary from about 0.05% w/v to about 5% w/v without effecting solubility in the formulation. In certain embodiments, the formulation comprises a sodium deoxycholate concentration of about 0.05% w/v. Alternatively, the formulation comprises a sodium deoxycholate concentration of about 0.07% w/v, or alternatively, about 0.1% w/v, or alternatively, about 0.3% w/v, or alternatively, about 0.5% w/v, or alternatively, about 0.7% w/v, or alternatively, about 1% w/v, or alternatively, about 2% w/v, or alternatively, about 3% w/v, or alternatively, about 4% w/v, or alternatively, about 5% w/v.

EXAMPLES

In the examples and elsewhere in the specification, abbreviations have the following meanings:
$A_{500}$=Absorbance at 500 Nanometers
cc=Cubic centimeter
Cm=Centimeter
F/T=Freeze/Thaw
HPLC=High-Performance Liquid Chromatography
hr.=Hour
mg=Milligram
mL=Milliliter
mm=Millimeter
mM=Millimolar
nm=Nanometer
t=Time
UV=Ultraviolet
v/v=Volume/Volume
w/v=Weight/Volume (g/mL)
w/w=Weight/Weight
WFI=Water for Injection The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Although several embodiments of the invention are described herein in detail, it will be understood by those skilled in the art that variations may be made thereto without departing from the spirit of the invention or the scope of the appended claims. Such modifications fall within the scope of the appended claims.

Example 1

Changes in pH and Visual Observations

This example demonstrates that aqueous formulations containing less than 5% w/v sodium deoxycholate forms a precipitate at various temperatures which cannot be brought back into solution. Solubility was best in aqueous formulations containing 5% w/v.

The stability of three lots of sodium deoxycholate dissolved in 0.9% benzyl alcohol and water for injection (WFI) was examined for changes in pH and visual observations, such as the formation of precipitate. Each lot was formulated at four concentrations: 5, 50, 100 and 160 mg/mL (0.5, 5, 10 and 16% w/v, respectively) dissolved in 0.9% benzyl alcohol and WFI. Table 1 provides a summary of the variables that were tested in this example.

TABLE 1

| Experimental Variables | | |
|---|---|---|
| Sample (Lot) Number | Sodium Deoxycholate Concentration (mg/mL) | % Weight/Volume (% w/v) |
| 1A | 5 | 0.5 |
| 1B | 50 | 5 |
| 1C | 100 | 10 |
| 1D | 160 | 16 |
| 2A | 5 | 0.5 |
| 2B | 50 | 5 |

TABLE 1-continued

Experimental Variables

| Sample (Lot) Number | Sodium Deoxycholate Concentration (mg/mL) | % Weight/Volume (% w/v) |
|---|---|---|
| 2C | 100 | 10 |
| 2D | 160 | 16 |
| 3A | 5 | 0.5 |
| 3B | 50 | 5 |
| 3C | 100 | 10 |
| 3D | 160 | 16 |
| 4 | 0 | 0 |

The solutions were prepared as follows. Two samples for each condition were filled at 2.0 mL into sterile 3 c.c. glass vials (West Pharma P/N 68000316), and stoppered with sterile 13 mm serum stoppers (West Pharma P/N 19560001). These samples were analyzed in duplicate at each time point in order to verify any changes in pH and visual observations, during storage at 2-8° C. and 25° C. for two weeks. Table 2 summarizes the conditions and time points at which samples were analyzed throughout the study.

TABLE 2

Conditions and Time Points

| Storage Conditions | Time Point Analyses | Analytical Methods |
|---|---|---|
| 2-8° C. | 1, 7, 14 days | pH and visual observation |
| 25° C. | 0, 1, 7, 14 days | pH and visual observation |

As seen in Tables 3 and 4, at 5 mg/mL (0.5% w/v), fine particulates were seen generally across all lots and at both 4° C. and 25° C., though Sample 1 at 4° C. did not precipitate. At 50 mg/mL (5% w/v), all samples and conditions were clear. At 100 mg/mL (10% w/v), there was a temperature effect as all lots at 4° C. precipitated out while the 25° C. lots remained clear. At 160 mg/mL (16% w/v), there was a temperature effect as all lots at 4° C. precipitated out while the 25° C. lots remained clear. The precipitation observed at 160 mg/mL (16% w/v) was more severe and rapid than 100 mg/mL, however, the precipitated product at these two concentrations could be resolubilized after warming to room temperature and vortexing. The precipitated material at 5 mg/mL (0.5% w/v) could not be brought back into solution. This data is shown graphically in FIGS. 1A to 1F.

The pH profiles for both 4° C. and 25° C. were overlapping, so it appears that temperature did not have an impact at concentrations less than 50 mg/mL (5% w/v). Instead, there appears to be a solubility pH for formulations less than 50 mg/mL (5% w/v). At 100 and 160 mg/mL, the 4° C. samples had a higher pH than the 25° C. samples. However, with increasing concentration, temperature appears to become more important than pH, and the formulation is increasingly sensitive to temperature.

TABLE 3 pH over Time at 4° C. (Average of Two Observations)

| Sample (Lot) Number | Sodium Deoxycholate Concentration | % Weight/Volume (% w/v) | 0 days | 1 day | 7 days | 14 days |
|---|---|---|---|---|---|---|
| 1A | 5 mg/mL | 0.5 | 7.565 | 7.56 | 7.625 | 7.67 |
| 1B | 50 mg/mL | 5 | 7.885 | 7.905 | 7.95 | 7.965 |
| 1C | 100 mg/mL | 10 | 7.89 | 7.93 | 7.995 | 8 |
|  |  |  |  |  | Precipitate | Precipitate |
| 1D | 160 mg/mL | 16 | 7.865 | 8.14 | 8.045 | 8.055 |
|  |  |  |  | Precipitate | Precipitate | Precipitate |
| 2A | 5 mg/mL | 0.5 | 7.62 | 7.53 | 7.6 | 7.66 |
|  |  |  | Precipitate | Precipitate | Precipitate |  |
| 2B | 50 mg/mL | 5 | 7.775 | 7.835 | 7.865 | 7.88 |
| 2C | 100 mg/mL | 10 | 7.77 | 7.845 | 7.98 | 7.93 |
|  |  |  |  | Precipitate | Precipitate | Precipitate |
| 2D | 160 mg/mL | 16 | 7.745 | 8 | 8.15 | 7.975 |
|  |  |  |  | Precipitate | Precipitate | Precipitate |
| 3A | 5 mg/mL | 0.5 | 7.625 | 7.61 | 7.715 | 7.74 |
|  |  |  |  | Precipitate | Precipitate | Precipitate |
| 3B | 50 mg/mL | 5 | 7.91 | 7.945 | 7.99 | 8 |
| 3C | 100 mg/mL | 10 | 7.905 | 7.97 | 7.99 | 8.01 |
|  |  |  |  |  | Precipitate | Precipitate |
| 3D | 160 mg/mL | 16 | 7.86 | 8.115 | 8.15 | 8.065 |
|  |  |  |  | Precipitate | Precipitate | Precipitate |
| 4 | 0 Placebo | 0 | 6.945 | 7.08 | 7.13 | 6.87 |

TABLE 4 pH over Time at 25° C. (Average of Two Observations)

| Sample (Lot) Number | Sodium Deoxycholate Concentration | % Weight/ Volume (% w/v) | 0 days | 1 day | 7 days | 14 days |
|---|---|---|---|---|---|---|
| 1A | 5 mg/mL | 0.5 | 7.565 | 7.595 Precipitate | 7.7 Precipitate | 7.73 Precipitate |
| 1B | 50 mg/mL | 5 | 7.885 | 7.95 | 7.95 | 7.98 |
| 1C | 100 mg/mL | 10 | 7.89 | 7.955 | 7.945 | 7.975 |
| 1D | 160 mg/mL | 16 | 7.865 | 7.94 | 7.935 | 7.93 |
| 2A | 5 mg/mL | 0.5 | 7.62 | 7.56 Precipitate | 7.665 Precipitate | 7.69 Precipitate |
| 2B | 50 mg/mL | 5 | 7.775 | 7.845 | 7.865 | 7.885 |
| 2C | 100 mg/mL | 10 | 7.77 | 7.85 | 7.865 | 7.875 |
| 2D | 160 mg/mL | 16 | 7.745 | 7.815 | 7.865 | 7.83 |
| 3A | 5 mg/mL | 0.5 | 7.625 | 7.63 Precipitate | 7.71 Precipitate | 7.76 Precipitate |
| 3B | 50 mg/mL | 5 | 7.91 | 7.955 | 7.985 | 8.015 |
| 3C | 100 mg/mL | 10 | 7.905 | 7.965 | 7.98 | 8.005 |
| 3D | 160 mg/mL | 16 | 7.86 | 7.965 | 7.955 | 7.975 |
| 4 | 0 Placebo | 0 | 6.945 | 6.825 | 6.945 | 6.93 |

Table 5 shows that the solubility of sodium deoxycholate is independent of the lot to lot variability in pH. In general, there was no difference in physical stability across lots under like conditions.

TABLE 5 pH by Sample over Time

| Sample (Lot) Number- Temperature | Sodium Deoxycholate Concentration | % Weight/ Volume (% w/v) | 0 days | 1 day | 7 days | 14 days |
|---|---|---|---|---|---|---|
| 1A-4° C. | 5 mg/mL | 0.5 | 7.565 | 7.56 | 7.625 | 7.67 |
| 2A-4° C. | 5 mg/mL | 0.5 | 7.62 | 7.53 | 7.6 | 7.66 |
| 3A-4° C. | 5 mg/mL | 0.5 | 7.625 | 7.61 | 7.715 | 7.74 |
| 1B-4° C. | 50 mg/mL | 5 | 7.885 | 7.905 | 7.95 | 7.965 |
| 2B-4° C. | 50 mg/mL | 5 | 7.775 | 7.835 | 7.865 | 7.88 |
| 3B-4° C. | 50 mg/mL | 5 | 7.91 | 7.945 | 7.99 | 8 |
| 1C-4° C. | 100 mg/mL | 10 | 7.89 | 7.93 | 7.995 | 8 |
| 2C-4° C. | 100 mg/mL | 10 | 7.77 | 7.845 | 7.98 | 7.93 |
| 3C-4° C. | 100 mg/mL | 10 | 7.905 | 7.97 | 7.99 | 8.01 |
| 1D-4° C. | 160 mg/mL | 16 | 7.865 | 8.14 | 8.045 | 8.055 |
| 2D-4° C. | 160 mg/mL | 16 | 7.745 | 8 | 8.15 | 7.975 |
| 3D-4° C. | 160 mg/mL | 16 | 7.86 | 8.115 | 8.15 | 8.065 |
| 1A-25° C. | 5 mg/mL | 0.5 | 7.565 | 7.595 | 7.7 | 7.73 |
| 2A-25° C. | 5 mg/mL | 0.5 | 7.62 | 7.56 | 7.665 | 7.69 |
| 3A-25° C. | 5 mg/mL | 0.5 | 7.625 | 7.63 | 7.71 | 7.76 |
| 1B-25° C. | 50 mg/mL | 5 | 7.885 | 7.95 | 7.95 | 7.98 |
| 2B-25° C. | 50 mg/mL | 5 | 7.775 | 7.845 | 7.865 | 7.885 |
| 3B-25° C. | 50 mg/mL | 5 | 7.91 | 7.955 | 7.985 | 8.015 |
| 1C-25° C. | 100 mg/mL | 10 | 7.89 | 7.955 | 7.945 | 7.975 |
| 2C-25° C. | 100 mg/mL | 10 | 7.77 | 7.85 | 7.865 | 7.875 |
| 3C-25° C. | 100 mg/mL | 10 | 7.905 | 7.965 | 7.98 | 8.005 |
| 1D-25° C. | 160 mg/mL | 16 | 7.865 | 7.94 | 7.935 | 7.93 |
| 2D-25° C. | 160 mg/mL | 16 | 7.745 | 7.815 | 7.865 | 7.83 |
| 3D-25° C. | 160 mg/mL | 16 | 7.86 | 7.965 | 7.955 | 7.975 |

Three factors have been identified to contribute to solubility. In no particular order these are concentration, pH and temperature. It has been found that the lot to lot variability in pH does not account for better or poorer solubility. Overall, the 50 mg/mL seems to be the most robust condition, where all lots appear to be above the "solubility" pH, and where temperature has no impact within the two-week time frame of this study. The results suggest that concentration, pH, and storage temperature factor into the stability of sodium deoxycholate. The samples at 50 mg/mL showed the best stability at 4° C. and 25° C. for two weeks.

Example 2

Stability Study

This example demonstrates that aqueous formulations of less than 5% w/v sodium deoxycholate at a pH of 8.0 to 8.5 exhibited very good solubility. This example also demonstrates that sodium deoxycholate shows no degradation in aqueous formulations having less than 5% w/v sodium deoxycholate during storage for eight weeks at 4° C., 25° C. and 37° C. A number of formulations were subjected to agitation, UV exposure, and freeze-thaw cycles and exhibited no degradation or precipitation when exposed to those stresses.

A two-month stability study of sodium deoxycholate in several different formulations was conducted. By reverse phase HPLC, sodium deoxycholate showed no degradation in all formulations at all temperatures. However, solubility was best in formulations containing 10 mM phosphate, 0.9% NaCl, 0.9% Benzyl Alcohol at a pH of 8.0 or 8.5. Storage temperatures of 25° C. and 37° C. also assisted solubility. All formulations that were chosen for agitation, UV exposure, and freeze—thaw exhibited no degradation or precipitation when exposed to those stresses.

Table 6 provides a list of chemicals used in the preparation of the formulations disclosed herein.

TABLE 6

Chemicals used in formulation preparation

| Chemical | Manufacturer (Product Number) | Grade |
| --- | --- | --- |
| Benzyl Alcohol | J. T. Baker (9041-01) | N.F./Multi Compendial |
| Sodium Chloride | EMD Chemicals (7760) | Molecular Biology Grade (99.95% pure) |
| Sodium Hydroxide Pellets | J. T. Baker (3728-01) | N.F./F.C.C. |
| Sodium Phosphate Monobasic, Monohydrate | J. T. Baker (3820-01) | U.S.P./F.C.C. |
| Sorbitol (Extra Pure) | EM Science (0035835B) | N.F./Ph. Eur. |

Stability Studies

The stability of the sodium deoxycholate formulations was examined at the conditions summarized in Table 7. Reverse phase HPLC was used along with visual observations which were conducted at each time point to monitor any precipitation or cloudiness. The formulations tested for vortex, UV exposure, and freeze-thaw, were chosen from the formulations that performed the best in the temperature study. The major stability issues of sodium deoxycholate observed during this study were solubility and pH drift.

TABLE 7

Stresses and time points

| Stress | Conditions | Time Points |
| --- | --- | --- |
| Temperature | 4° C. | 0, 2 weeks, 1 and 2 months |
|  | 25° C. | 0, 2 weeks, 1 and 2 months |
|  | 37° C. | 0, 2 weeks, 1 and 2 months |
| Agitation | Vortex | 4 hours |
| Light | UV exposure | 24 hours |
| Freeze-Thaw | −70° C. to 25° C. | 5 cycles | i. Effect of Temperature on Stability

The formulations were incubated at 4° C., 25° C. and 37° C. and analyzed for a) degradation products, b) pH stability and c) formulation clarity.

Formulations Tested

Except for formulations only consisting of water, sodium deoxycholate was dissolved in buffer that had been titrated to a pH of 6. Each formulation, except for the two only consisting of water, was then titrated to its target pH with NaOH. All formulations were sterile filtered and filled to 1.5 mL in sterile 2 cc glass vials. The filled vials were then autoclaved. The formulations 3A and 3B were cloudy prior to filling.

TABLE 8

List of Formulations

| Formulation | Buffer | Excipient(s) | pH | Sodium Deoxycholate Concentration (mg/mL) | % Weight/Volume (% w/v) |
| --- | --- | --- | --- | --- | --- |
| 1A WFI20 | None | WFI only | — | 20 | 2 |
| 1B WFI5 | None | WFI only | — | 5 | 0.5 |
| 2A P7.5NB20 | 10 mM phosphate | 0.9% NaCl; 0.9% Benzyl Alcohol | 7.5 | 20 | 2 |
| 2B P7.5NB5 | 10 mM phosphate | 0.9% NaCl; 0.9% Benzyl Alcohol | 7.5 | 5 | 0.5 |
| 3A P7.5SB20 | 10 mM phosphate | 5% Sorbitol; 0.9% Benzyl Alcohol | 7.5 | 20 | 2 |
| 3B P7.5SB5 | 10 mM phosphate | 5% Sorbitol; 0.9% Benzyl Alcohol | 7.5 | 5 | 0.5 |
| 4A P8NB20 | 10 mM phosphate | 0.9% NaCl; 0.9% Benzyl Alcohol | 8.0 | 20 | 2 |
| 4B P8NB5 | 10 mM phosphate | 0.9% NaCl; 0.9% Benzyl Alcohol | 8.0 | 5 | 0.5 |
| 4C P8NB10 | 10 mM phosphate | 0.9% NaCl; 0.9% Benzyl Alcohol | 8.0 | 10 | 1 |
| 5 P8N5 | 10 mM phosphate | 0.9% NaCl | 8.0 | 5 | 0.5 |
| 6A P8SB20 | 10 mM phosphate | 5% Sorbitol; 0.9% Benzyl Alcohol | 8.0 | 20 | 2 |
| 6B P8SB5 | 10 mM phosphate | 5% Sorbitol; 0.9% Benzyl Alcohol | 8.0 | 5 | 0.5 |

TABLE 8-continued

List of Formulations

| Formulation | Buffer | Excipient(s) | pH | Sodium Deoxycholate Concentration (mg/mL) | % Weight/Volume (% w/v) |
|---|---|---|---|---|---|
| 7 P8S5 | 10 mM phosphate | 5% Sorbitol | 8.0 | 5 | 0.5 |
| 8A P8.5NB20 | 10 mM phosphate | 0.9% NaCl; 0.9% Benzyl Alcohol | 8.5 | 20 | 2 |
| 8B P8.5NB5 | 10 mM phosphate | 0.9% NaCl; 0.9% Benzyl Alcohol | 8.5 | 5 | 0.5 |
| 9A P8.5SB20 | 10 mM phosphate | 5% Sorbitol; 0.9% Benzyl Alcohol | 8.5 | 20 | 2 |
| 9B P8.5SB5 | 10 mM phosphate | 5% Sorbitol; 0.9% Benzyl Alcohol | 8.5 | 5 | 0.5 | a) Degradation Products

Figure 3:
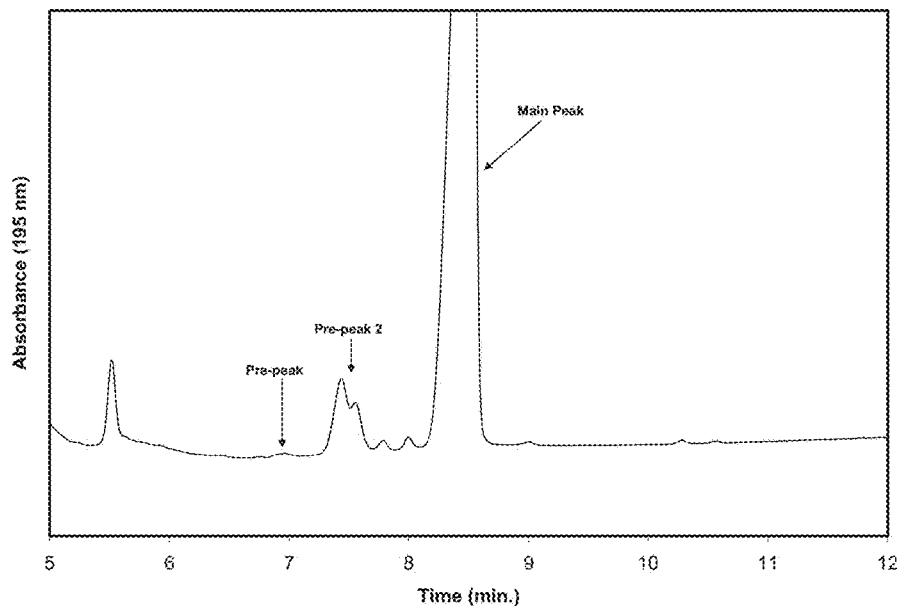
FIG. 3 shows a reverse phase HPLC chromatogram for a 20 mg/mL (2% w/v) aqueous formulation of sodium deoxycholate (0.9% NaCl and 0.9% benzyl alcohol in 10 mM phosphate buffer at a pH of 8.0) after being incubated for 2 months at 4° C.
Figure 4:
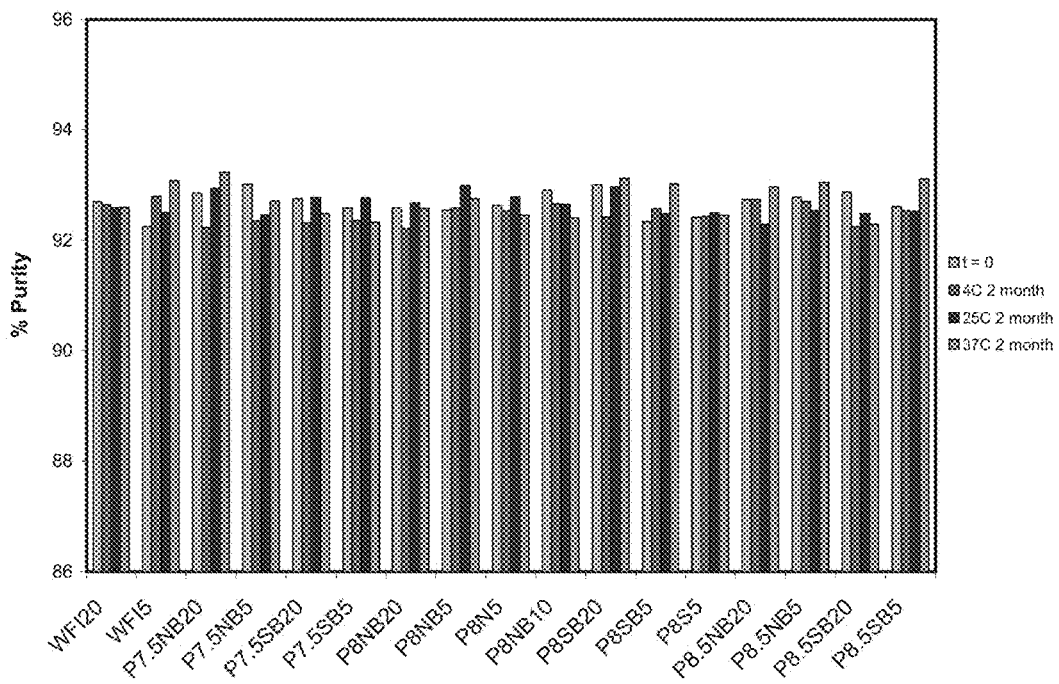
FIG. 4 shows the effect of temperature (4° C., 25° C. and 37° C.) on the purity of various sodium deoxycholate formulations of over a two month period.

Reverse phase HPLC was used to visualize degradation products. A sample chromatogram of formulation 4A shows the main peak with respect to the degradation products (FIG. 3). FIG. 4 shows the main peak with respect to the degradation products (i.e. Purity) for all formulations at the incubation temperatures of 4° C., 25° C. and 37° C. FIG. 4 shows the purity at t=0 and 2 months. The results suggest that no chemical degradation occurred in any of the formulations of Table 8.

b) pH Stability

Table 9 shows the pH of the formulations prior to filling and at t=0. In general, the pH drifted towards 8 and remained constant throughout the study. This suggests that sodium deoxycholate has some buffering capacity.

TABLE 9 pH Drift

| Formulation | pH prior to fill | pH at t = 0 |
|---|---|---|
| WFI20 | 8.1 | 8.3 |
| WFI5 | 7.2 | 7.5 |
| P7.5NB20 | 7.5 | 7.7 |
| P7.5NB5 | 7.5 | 7.8 |
| P7.5SB20 | 7.5 | 7.6 |
| P7.5SB5 | 7.4 | 7.6 |
| P8NB20 | 8.0 | 8.3 |
| P8NB5 | 8.0 | 8.3 |
| P8N5 | 8.1 | 8.5 |
| P8NB10 | 8.0 | 8.2 |
| P8SB20 | 7.9 | 8.0 |
| P8SB5 | 8.0 | 7.8 |
| P8S5 | 8.0 | 7.9 |
| P8.5NB20 | 8.5 | 8.3 |
| P8.5NB5 | 8.5 | 8.5 |
| P8.5SB20 | 8.5 | 8.1 |
| P8.5SB5 | 8.5 | 8.0 | c) Formulation Clarity

The clarity of each formulation was determined by two methods. One method was by visual observation, where the vial was held up to an intense light and the presence of particles was determined by what the eye could see. A set of vials filled with the formulation buffers and incubated at the three temperatures where used as reference standards. The other method used light scattering by illuminating the samples across a 1 cm path length with 500 nm light in a spectrophotometer.

The presence of visible precipitates in some formulations increased over time, particularly at 4° C. The formulations containing sorbitol at the lowest pH produced the most precipitation. The formulations that performed the best contained 10 mM phosphate, 0.9% NaCl, 0.9% Benzyl Alcohol at pH 8.0 or 8.5.

Tables 10, 11, 12 and 13 show the clarity results. The "Visual Clarity" column has a ranking system as follows: 0=clear, no particles; 1=clear, few particles; 2=clear, several particles; 3=clear, many large particles, 4=slightly cloudy; 5=very cloudy.

TABLE 10 t = 0

| Formulation | Visual Clarity | Comments | $A_{500}$ |
|---|---|---|---|
| WFI20 | 0 | | 0.0064 |
| WFI5 | 0 | | 0.0103 |
| P7.5NB20 | 0 (gelatinous) | | 0.0467 |
| P7.5NB5 | 0 | | 0.0042 |
| P7.5SB20 | 0 (gelatinous) | | 0.0405 |
| P7.5SB5 | 3 | Many large particles | 0.1599 |
| P8NB20 | 0 | | 0.0076 |
| P8NB5 | 0 | | 0.0059 |
| P8N5 | 0 | | 0.0053 |
| P8NB10 | 0 | | 0.0038 |
| P8SB20 | 0 | | 0.0067 |
| P8SB5 | 0 | | 0.0426 |
| P8S5 | 0 | | 0.0099 |
| P8.5NB20 | 0 | | 0.0012 |
| P8.5NB5 | 0 | | 0.0048 |
| P8.5SB20 | 0 | | 0.0130 |
| P8.5SB5 | 0 | | 0.0230 |

TABLE 11

4° C., 2 months

| Formulation | Visual Clarity | Comments | $A_{500}$ |
|---|---|---|---|
| WFI20 | 0 | | −0.0006 |
| WFI5 | 2 | Precipitate | 0.0037 |
| P7.5NB20 | 0 | Gelatinous | −0.0001 |
| P7.5NB5 | 0 | | −0.0036 |
| P7.5SB20 | 3 | Precipitate | 0.0340 |
| P7.5SB5 | 3 | Precipitate | 0.2009 |
| P8NB20 | 2 | Possible precipitate | −0.0006 |
| P8NB5 | 0 | | −0.0019 |
| P8N5 | 1 | Similar to buffer | 0.0019 |
| P8NB10 | 0 | | 0.0124 |

TABLE 11-continued

4° C., 2 months

| Formulation | Visual Clarity | Comments | $A_{500}$ |
|---|---|---|---|
| P8SB20 | 2 | Possible precipitate | 0.0151 |
| P8SB5 | 2 | Precipitate | 0.0207 |
| P8S5 | 0 | | 0.0156 |
| P8.5NB20 | 0 | | 0.0147 |
| P8.5NB5 | 1 | Similar to buffer | 0.0156 |
| P8.5SB20 | 1 | Similar to buffer | 0.0190 |
| P8.5SB5 | 0 | | 0.0223 |

TABLE 12

25° C., 2 months

| Formulation | Visual Clarity | Comments | $A_{500}$ |
|---|---|---|---|
| WFI20 | 0 | | 0.0078 |
| WFI5 | 2 | Precipitate | 0.0102 |
| P7.5NB20 | 0 | | 0.0081 |
| P7.5NB5 | 0 | | 0.0161 |
| P7.5SB20 | 4 | Precipitate | 0.2129 |
| P7.5SB5 | 4 | Precipitate | 0.1659 |
| P8NB20 | 0 | | 0.0179 |
| P8NB5 | 1 | Similar to buffer | 0.0200 |
| P8N5 | 0 | | 0.0189 |
| P8NB10 | 1 | Similar to buffer | 0.0161 |
| P8SB20 | 0 | | 0.0183 |
| P8SB5 | 2 | Possible precipitate | 0.0262 |
| P8S5 | 1 | Similar to buffer | 0.0184 |
| P8.5NB20 | 0 | | 0.0208 |
| P8.5NB5 | 1 | Similar to buffer | 0.0195 |
| P8.5SB20 | 0 | | 0.0254 |
| P8.5SB5 | 1 | Similar to buffer | 0.0229 |

TABLE 13

37° C., 2 months

| Formulation | Visual Clarity | Comments | $A_{500}$ |
|---|---|---|---|
| WFI20 | 0 | | 0.0187 |
| WFI5 | 2 | Precipitate | 0.0266 |
| P7.5NB20 | 0 | | 0.0196 |
| P7.5NB5 | 0 | | 0.0225 |
| P7.5SB20 | 4 | Precipitate | 0.4785 |
| P7.5SB5 | 4 | Precipitate | 0.6743 |
| P8NB20 | 0 | | 0.0046 |
| P8NB5 | 0 | | −0.0016 |
| P8N5 | 1 | Similar to buffer | 0.0047 |
| P8NB10 | 0 | | −0.0012 |
| P8SB20 | 0 | | 0.0037 |
| P8SB5 | 2 | Possible precipitate | 0.0195 |
| P8S5 | 0 | | 0.0086 |
| P8.5NB20 | 0 | | 0.0013 |
| P8.5NB5 | 0 | | 0.0039 |
| P8.5SB20 | 0 | | 0.0056 |
| P8.5SB5 | 1 | Similar to buffer | 0.0040 | ii. Effects of Agitation, UV Exposure, and Freeze-Thaw on Stability

Based on the results from the temperature study, the following formulations in Table 14 were chosen to test the effects of Agitation, UV Exposure, and Freeze-Thaw on stability.

TABLE 14

Agitation, UV Exposure, and Freeze - Thaw Formulations

| Formulation | Buffer | Excipients | pH | Concentration (mg/mL) | % Weight/Volume (% w/v) |
|---|---|---|---|---|---|
| 4A P8NB20 | 10 mM phosphate | 0.9% NaCl; 0.9% Benzyl Alcohol | 8.0 | 20 | 2 |
| 4C P8NB10 | 10 mM phosphate | 0.9% NaCl; 0.9% Benzyl Alcohol | 8.0 | 10 | 1 |
| 4B P8NB5 | 10 mM phosphate | 0.9% NaCl; 0.9% Benzyl Alcohol | 8.0 | 5 | 0.5 |
| 8A P8.5NB20 | 10 mM phosphate | 0.9% NaCl; 0.9% Benzyl Alcohol | 8.5 | 20 | 2 |
| 8C P8.5NB10 | 10 mM phosphate | 0.9% NaCl; 0.9% Benzyl Alcohol | 8.5 | 10 | 1 |
| 8B P8.5NB5 | 10 mM phosphate | 0.9% NaCl; 0.9% Benzyl Alcohol | 8.5 | 5 | 0.5 | a) Degradation Products

Figure 5:
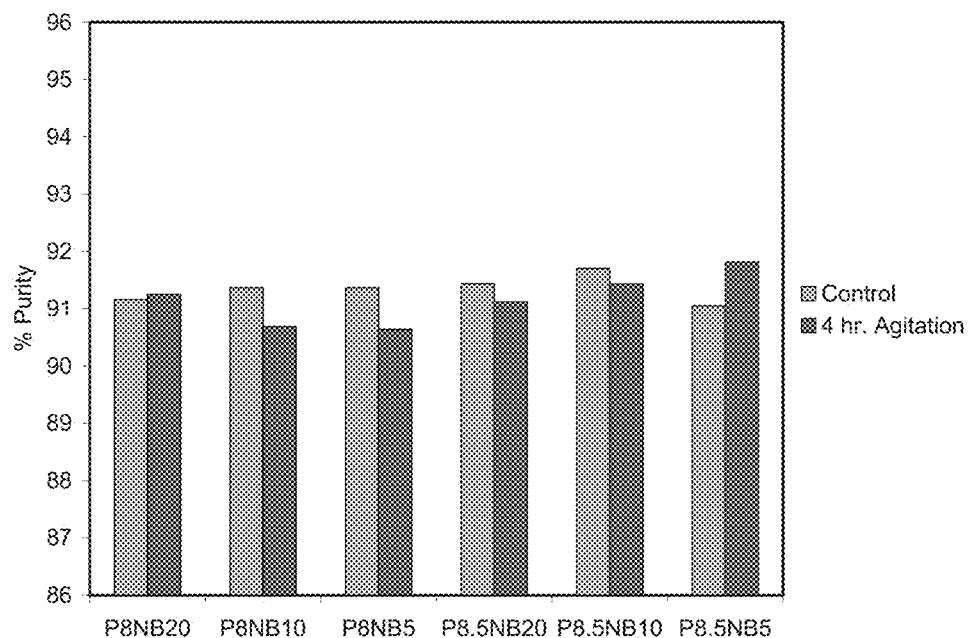
FIG. 5 shows the effect of agitation on the purity of various sodium deoxycholate formulations of over a four hour period.
Figure 6:
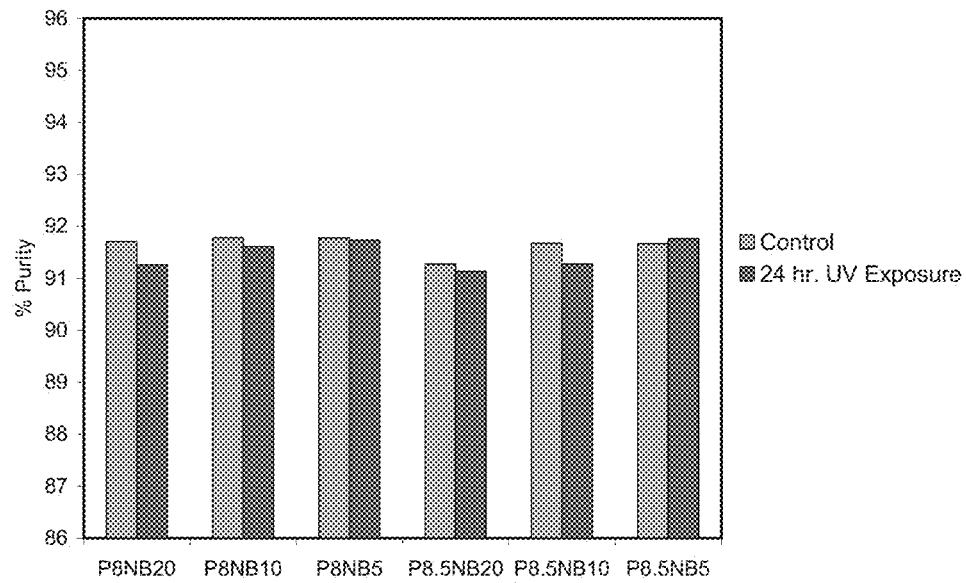
FIG. 6 shows the effect of UV exposure on the purity of various sodium deoxycholate formulations of over a 24 hour period.
Figure 7:
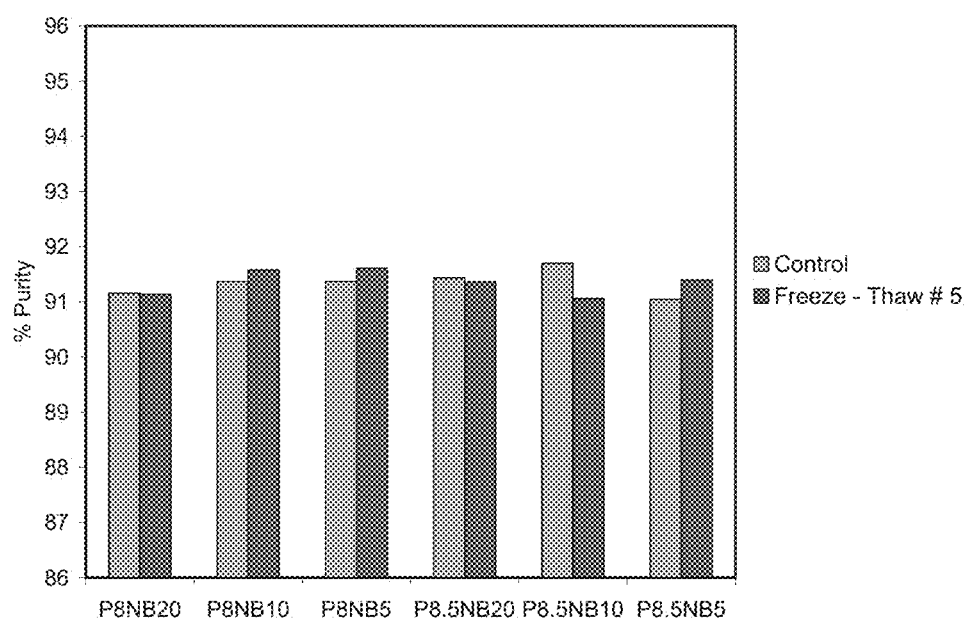
FIG. 7 shows the effect of five freeze-thaw cycles on the purity of various sodium deoxycholate formulations.

Reverse phase HPLC was used to visualize degradation products. FIGS. 5, 6 and 7 show the main peak with respect to the degradation products (i.e. Purity) for the formulations in Table 14 under the stress of agitation, UV exposure, and five freeze-thaw cycles. The results suggest that no chemical degradation occurred as a result of any of the stresses.

b) pH Stability

Table 15 shows the pH of the formulations prior to filling different than the pH's after opening the vials.

TABLE 15 pH Stability

| Formulation | pH Prior to Fill | pH at t = 0 |
|---|---|---|
| 4A P8NB20 | 8.0 | 7.8 |
| 4C P8NB10 | 8.0 | 7.9 |
| 4B P8NB5 | 8.0 | 7.9 |
| 8A P8.5NB20 | 8.5 | 8.3 |
| 8C P8.5NB10 | 8.5 | 8.2 |
| 8B P8.5NB5 | 8.5 | 8.1 | c) Formulation Clarity

The clarity of each formulation was determined by two methods. One method was by visual observation, where the vial was held up to an intense light and the presence of particles was determined by what the eye could see. A set of vials filled with the formulation buffers and incubated at the three temperatures where used as reference standards. The other method used light scattering by illuminating the samples across a 1 cm path length with 500 nm light in a spectrophotometer.

Agitation, UV exposure, and freeze-thaw cycles does not appear to induce precipitation.

Tables 16, 17 and 18 show the clarity results. The "Visual Clarity" column has a ranking system as follows: 0=clear, no particles; 1=clear, few particles; 2=clear, several particles; 3=clear, many large particles, 4=slightly cloudy; 5=very cloudy.

TABLE 16

Agitation

| Formulation | Stress | Visual Clarity | Comments | $A_{500}$ |
|---|---|---|---|---|
| 4A P8NB20 | Control | 1 | Similar to buffer | 0.0023 |
| P8NB20 | 4 hr. | 0 | | 0.0068 |
| 4C P8NB10 | Control | 0 | | −0.0001 |
| P8NB10 | 4 hr. | 0 | | 0.0079 |
| 4B P8NB5 | Control | 0 | | 0.0002 |
| P8NB5 | 4 hr. | 0 | | 0.0019 |
| 8A P8.5NB20 | Control | 0 | | −0.0002 |
| P8.5NB20 | 4 hr. | 0 | | 0.0024 |
| 8C P8.5NB10 | Control | 1 | Similar to buffer | 0.0087 |
| P8.5NB10 | 4 hr. | 1 | Similar to buffer | 0.0010 |
| 8B P8.5NB5 | Control | 1 | Similar to buffer | 0.0029 |
| P8.5NB5 | 4 hr. | 0 | | 0.0022 |

TABLE 17

UV Exposure

| Formulation | Stress | Visual Clarity | Comments | $A_{500}$ |
|---|---|---|---|---|
| 4A P8NB20 | Control | 0 | | 0.0039 |
| P8NB20 | 24 hr. | 0 | | 0.0023 |
| 4C P8NB10 | Control | 1 | Similar to buffer | 0.0009 |
| P8NB10 | 24 hr. | 1 | Similar to buffer | 0.0011 |
| 4B P8NB5 | Control | 0 | | 0.0020 |
| P8NB5 | 24 hr. | 1 | Similar to buffer | 0.0017 |
| 8A P8.5NB20 | Control | 0 | | 0.0046 |
| P8.5NB20 | 24 hr. | 0 | | 0.0072 |
| 8C P8.5NB10 | Control | 1 | Similar to buffer | 0.0121 |
| P8.5NB10 | 24 hr. | 0 | | 0.0023 |
| 8B P8.5NB5 | Control | 1 | Similar to buffer | 0.0027 |
| P8.5NB5 | 24 hr. | 0 | | 0.0029 |

TABLE 18

Freeze - Thaw Cycles

| Formulation | Stress | Visual Clarity | Comments | $A_{500}$ |
|---|---|---|---|---|
| 4A P8NB20 | t = 0 | 1 | Similar to buffer | 0.0023 |
| P8NB20 | F/T 5 | 0 | | 0.0084 |
| 4C P8NB10 | t = 0 | 0 | | −0.0001 |
| P8NB10 | F/T 5 | 0 | | 0.0064 |
| 4B P8NB5 | t = 0 | 0 | | 0.0002 |
| P8NB5 | F/T 5 | 0 | | 0.0022 |
| 8A P8.5NB20 | t = 0 | 0 | | −0.0002 |
| P8.5NB20 | F/T 5 | 0 | | 0.0161 |
| 8C P8.5NB10 | t = 0 | 1 | Similar to buffer | 0.0087 |
| P8.5NB10 | F/T 5 | 0 | | −0.0005 |
| 8B P8.5NB5 | t = 0 | 1 | Similar to buffer | 0.0029 |
| P8.5NB5 | F/T 5 | 0 | | −0.0036 |

After screening the stability profile of sodium deoxycholate in seventeen unique formulations, it was determined that formulations containing 10 mM Phosphate, 0.9% NaCl and 0.9% Benzyl Alcohol at pH 8.0 or 8.5 best prevented visible precipitation in addition to maximizing solubility. By reverse phase HPLC, sodium deoxycholate shows no degradation in all formulations at all temperatures, during storage for eight weeks at 4° C., 25° C. and 37° C. As far as visual clarity of formulations, storage temperatures of 25° C. and 37° C. actually improved the solubility of sodium deoxycholate as compared to 4° C.

All formulations that were chosen for agitation, UV exposure, and freeze-thaw exhibited no degradation or precipitation when exposed to those stresses. Upon completion of the eight week storage stability study, selected formulations were subjected to these acute stress conditions. These experiments help determine the stability of sodium deoxycholate during the stress of common manufacturing and shipping procedures. The data obtained from these acute stress studies confirm the stability of sodium deoxycholate in formulations containing 10 mM Phosphate, 0.9% NaCl and 0.9% Benzyl Alcohol at pH 8.0 or 8.5, with sodium deoxycholate concentration of 5, 10 and 20 mg/mL.

What is claimed is:

1. An aqueous pharmaceutical formulation consisting of about 0.05% w/v to about 2% w/v sodium deoxycholate, water, a phosphate buffer, a base, a preservative, and tonicity agent; wherein the formulation has a pH of from about 8.0 to about 8.5.

2. The aqueous pharmaceutical formulation of claim 1, wherein the aqueous formulation is suitable for subcutaneous injection.

3. The aqueous pharmaceutical formulation of claim 1, wherein the pH is about 8.3.

4. The aqueous pharmaceutical formulation of claim 1, wherein said preservative is benzyl alcohol.

5. The aqueous pharmaceutical formulation of claim 1, wherein said base is sodium hydroxide.

6. The aqueous pharmaceutical formulation of claim 1, wherein said tonicity agent is sodium chloride.

* * * * *